US008772037B2

(12) United States Patent
Satomura et al.

(10) Patent No.: US 8,772,037 B2
(45) Date of Patent: Jul. 8, 2014

(54) ANALYSIS ASSISTING METHOD, ANALYZER, REMOTE COMPUTER, DATA ANALYZING METHOD, PROGRAM, AND REAGENT CONTAINER

(75) Inventors: Masahiro Satomura, Hyogo (JP); Hishiri Komiyama, Osaka (JP)

(73) Assignee: Wako Pure Chemical Industries, Ltd., Osaka-Shi (JP)

( * ) Notice: Subject to any disclaimer, the term of this patent is extended or adjusted under 35 U.S.C. 154(b) by 1317 days.

(21) Appl. No.: 11/632,710

(22) PCT Filed: Jul. 22, 2005

(86) PCT No.: PCT/JP2005/013487
§ 371 (c)(1),
(2), (4) Date: Jan. 18, 2007

(87) PCT Pub. No.: WO2006/009251
PCT Pub. Date: Jan. 26, 2006

(65) Prior Publication Data
US 2007/0255756 A1 Nov. 1, 2007

(30) Foreign Application Priority Data

Jul. 22, 2004 (JP) ................................ 2004-214695

(51) Int. Cl.
*G01N 35/00* (2006.01)
*B01L 3/00* (2006.01)

(52) U.S. Cl.
CPC .... *G01N 35/00663* (2013.01); *G01N 35/00732* (2013.01); *G01N 35/00871* (2013.01); *B01L 3/545* (2013.01); *G01N 2035/00841* (2013.01)
USPC .................. 436/50; 436/43; 436/55; 422/63; 235/375

(58) Field of Classification Search
CPC .................. G01N 35/00871; G01N 35/00732; G01N 35/00663
See application file for complete search history.

(56) References Cited

U.S. PATENT DOCUMENTS 5,695,718 A 12/1997 Imai et al.
2001/0051952 A1 12/2001 Nakazato
(Continued)

FOREIGN PATENT DOCUMENTS

JP A 05-026881 2/1993
JP A 07-260793 10/1995
(Continued)

OTHER PUBLICATIONS

Oct. 19, 2010 Office Action issued in Japanese Patent Application No. 2006-529296 (with translation).
(Continued)

*Primary Examiner* — P. Kathryn Wright
(74) *Attorney, Agent, or Firm* — Oliff PLC

(57) ABSTRACT

In an analysis system having an analysis apparatus using a reagent container having a memory to store reagent information concerning the reagent in the reagent container and a remote computer, the following steps are executed: reading out the reagent information from the memory of the reagent container; judging, based on the read reagent information, whether or not the reagent in the reagent container is usable; when it is judged that the reagent in the reagent container is unusable, writing data representing the reagent is unusable into the memory of the reagent container; and when it is judged that the reagent in the reagent container is unusable, registering the data representing the reagent is unusable, into a reagent database managed by the remote computer in association with identification information to identify the reagent container. Thus, it is possible to automatically identify the reagent, which should not be used, and to manage the reagent not so as to use it for the analysis. In addition, it is possible to use the data for the enhancement of the business efficiency such as the automatic order of the reagent, the stock management in the manufacturer and the like.

10 Claims, 12 Drawing Sheets

(56) References Cited

U.S. PATENT DOCUMENTS

| | | |
|---|---|---|
| 2002/0128801 A1 | 9/2002 | Okuno et al. |
| 2004/0057872 A1 | 3/2004 | Shibuya et al. |
| 2005/0159982 A1* | 7/2005 | Showalter et al. ............... 705/2 |
| 2005/0170356 A1* | 8/2005 | Kureshy et al. ................. 435/6 |
| 2006/0190185 A1* | 8/2006 | Ford et al. ..................... 702/19 |

FOREIGN PATENT DOCUMENTS

| | | |
|---|---|---|
| JP | A 10-215494 | 8/1998 |
| JP | A 2001-229291 | 8/2001 |
| JP | 2003-279583 * | 10/2003 |
| JP | A 2003-279583 | 10/2003 |
| JP | A 2004-028670 | 1/2004 |
| WO | WO 02/059624 A1 | 8/2002 |
| WO | WO 03/100389 A1 | 12/2003 |
| WO | WO 03/102241 A1 | 12/2003 |

OTHER PUBLICATIONS

Feb. 15, 2012 Search Report issued in European Application No. 05761816.7.

* cited by examiner

| CONTENTS | DETAILS | PRESENCE OR ABSENCE OF INFO. UPDATE |
|---|---|---|
| INFO. CONCERNING PRODUCTION | PRODUCTION LOT NO.<br>SERIAL NO.<br>EXPIRATION DATE | NO<br>NO<br>NO |
| INFO. CONCERNING ANALYSIS CONDITION | PARAMETER<br>(SPECIMEN QUANTITY TO BE CONSUMED, REAGENT QUANTITY TO BE CONSUMED, MEASUREMENT WAVELENGTH(MAIN WAVELENGTH, SUB-WAVELENGTH), REACTION TIME, MEASUREMENT POINT)<br>CALIBRATION METHOD<br>(INCLUDING OPTIONAL INFO.)<br>DILUTION CONDITION<br>(KIND OF DILUENT, DILUTION RATE) | YES<br><br><br><br>YES<br><br>YES |
| INFO. CONCERNING REAGENT CAPABILITY | CALIBRATION INFO.<br>STRAIGHTNESS<br>REPEATABILITY<br>INFLUENCE OF COEXISTENT MATERIAL<br>REACTION TIME COURSE<br>STABILITY<br>THRESHOLD DATA | YES<br>YES<br>YES<br>YES<br>YES<br>YES<br>YES |
| INFO. CONCERNING DISPLAY | UNIT<br>NO. OF INDICATION DIGITS<br>REFERENCE VALUE(RANGE) | NO<br>NO<br>YES |
| INFO. CONCERNING RESULT | SERUM DATA<br>COMPUTING BETWEEN ITEMS<br>(ITEMS, COMPUTING EXPRESSION, UNIT, NO. OF DIGITS) | NO<br>YES |

FIG.4-1

| TIME | CONTENTS | DETAILS |
|---|---|---|
| INFO. WRITTEN IN USE AND OTHER TIME | INFO. CONCERNING KEEPING CONDITION etc. | TRANSPORTATION CONDITIONS (TEMPERATURE, HUMIDITY, TIME, VIBRATION)<br>KEEPING CONDITIONS (TEMPERATURE, HUMIDITY, TIME, VIBRATION) |
| INFO. WRITTEN IN USE | INFO. CONCERNING UTILIZATION CONDITION | NO. OF USED TIMES<br>DATE OF USE<br>TIME OF USE<br>EXPIRATION DATE<br>REMAINING AMOUNT<br>INFORMATION OF USABLENESS/UNUSABLENESS |
| | INFO. CONCERNING RESULT FILE | ENVIRONMENT INFORMATION<br>  MEASURING ANALYSIS APPARATUS ID, MEASUREMENT ITEMS, MEASUREMENT CONDITION, PARAMETERS AT MEASUREMENT, INFO. CONCERNING OBJECT TO BE EXAMINED, CELL BLANK VALUE AT MEASUREMENT, REACTION TIME COURSE AT MEASUREMENT, ANALYSIS RESULT<br>CAPABILITY INFORMATION<br>  MEASURED BLANK VALUE, INFO. OF CALIBRATION CARRIED OUT, CONTROL MEASUREMENT RESULT<br>ALARM INFORMATION |

FIG.4-2

| APPARATUS ID | DATA VALUE | \| DATA VALUE−AVERAGE VALUE \| | JUDGMENT |
|---|---|---|---|
| A | 150 | 46 | 1 |
| B | 100 | 4 | 5 |
| C | 105 | 1 | 5 |
| D | 110 | 6 | 5 |
| E | 92 | 12 | 4 |
| ⋮ | ⋮ | ⋮ | |
| Z | 99 | 5 | 5 |

FIG.11-1

| JUDGMENT | \| DATA VALUE−AVERAGE VALUE \| | REMARKS |
|---|---|---|
| 5 | LESS THAN 10 | NO DIFFERENCE BETWEEN APPARATUSES |
| 4 | EQUAL TO OR GREATER THAN 10 ~ LESS THAN 20 | NO DIFFERENCE BETWEEN APPARATUSES, MONITOR REQUIRED |
| 3 | EQUAL TO OR GREATER THAN 20 ~ LESS THAN 30 | ATTENTION REQUIRED |
| 2 | EQUAL TO OR GREATER THAN 30 ~ LESS THAN 40 | DETECTION OF DIFFERENCE BETWEEN APPARATUSES |
| 1 | EQUAL TO OR GREATER THAN 40 | DETECTION OF LARGE DIFFERENCE BETWEEN APPARATUSES |

FIG.11-2

ANALYSIS ASSISTING METHOD, ANALYZER, REMOTE COMPUTER, DATA ANALYZING METHOD, PROGRAM, AND REAGENT CONTAINER

FIELD OF THE INVENTION

This invention relates to a support technique for an analysis using a reagent.

BACKGROUND

For example, US-2001/0051952-A1 discloses a technique whose object is to provide an analysis apparatus capable of easily carrying out the backup, enhancing the reliability, reducing the work load for the information management and operation, shortening the recovery time, and easily controlling the management/operation between other apparatuses and further from a remote place. More specifically, a controller in the technique controls by using, as control conditions of the analysis apparatus, various information such as reagent information, measurement conditions, calibration curve data item definition information and the like. As for an information storage means, plural hard disk drives are provided or a hard disk drive is partitioned into plural partitions, and the backup is carried out according to a predetermined condition. In addition, by managing information by using a markup language, the remote maintenance is provided. Although it is possible to manage the reagent in the analysis apparatus, it is not considered that the useful information is held by the reagent itself to manage the reagent.

Moreover, JP-A-2004-28670 discloses a technique to take an examiner's analysis preparation work and the like, which is carried out in an examination facility via a communication means by a service company to reduce the work load of the examiner in the examination facility and stabilize the analysis preparation work and the like. More specifically, the examination facility that carries out analysis services by using an automatic analysis apparatus or the like; a service company that obtains data of the operation state or the like of the automatic analysis apparatus in real time via a communication line and carries out the service business such as an analysis and diagnosis of various data, maintenance and check and the like; and plural examiners carrying out an analysis work in an examination facility respectively have a means for communicating at any time via a communication means. Then, the service company remotely supports, via the communication line, the acting of the analysis preparation work as the analysis preparation work before the beginning of the analysis work in the facility, and the acting of the cell cleaning of the automatic analysis apparatus and the acting of the basic operation confirmation work, and reports the analysis preparation work and ending work to the examiner. Although a technique that the operation state or the like of the analysis apparatus is analyzed in a remote place is disclosed, it is not considered for the management of the reagent by holding the useful information by the reagent itself, and a processing to be carried out in a case where the useful information is held by the reagent itself.

Patent Document 1: US-2001/0051952-A1
Patent Document 2: JP-A-2004-28670

SUMMARY

Thus, there is no conventional art having the premise that information is held by the reagent itself (actually, a reagent container). In addition, even when the analysis apparatus is connected to a network, the reagent itself becomes separated. Therefore, there is a problem on the reagent management. Moreover, there is no prior technique enabling the management of the reagent and the analysis apparatus and the analysis support, which are useful for not only the reagent manufacturer and the maintenance service provider for the analysis apparatus, but also the users, before the analysis, during the analysis and after the analysis.

Therefore, an object of this invention is to provide a new reagent management technique in the case where data concerning the reagent in the reagent container is held by the reagent container itself.

In addition, another object of this invention is to provide a new analysis support technique in a case where the reagent is connected to a network.

An analysis support method according to a first aspect of this invention is a method executed by an analysis system having an analysis apparatus using a reagent container having a memory to store reagent information concerning the reagent in the reagent container and a remote computer (e.g. a host computer in an embodiment) connected with the analysis apparatus. The method includes: a step of reading out the reagent information from the memory of the reagent container; a judging step of judging, based on the read reagent information, whether or not the reagent in the reagent container is usable; when it is judged that the reagent in the reagent container is unusable, a step of writing data representing the reagent is unusable into the memory of the reagent container; and when it is judged that the reagent in the reagent container is unusable, a step of registering the data representing the reagent is unusable into a reagent database managed by the remote computer in association with identification information to identify the reagent container.

Thus, it is possible to automatically identify the reagent, which should not be used, and to manage the reagent and carry out a setting for the reagent not so as to use it for the analysis. In addition, by registering data representing the reagent is unusable also into the reagent database managed by the remote computer, it is also possible to use the data for the enhancement of the business efficiency such as the automatic order of the reagent, the stock management in the manufacturer and the like.

In addition, the method may further include: when it is judged at the judging step that the reagent in the reagent container is usable, a second judging step of judging, based on a condition as to whether or not the reagent is usable, whether or not the reagent in the reagent container is usable, wherein the condition is identified from utilization results of reagents having a predetermined relation with the reagent in the reagent container; and when it is judged at the second judging step that the reagent in the reagent container is unusable, a step of writing the data representing the reagent is unusable into the memory of the reagent container. Thus, by judging, based on the condition as to whether or not the reagent is usable, whether or not the reagent in the reagent container is usable, wherein the condition is identified from the utilization results of the reagents having a predetermined relation with the reagent in the reagent container (e.g. a condition that a reagent is included in a specific lot identified as a lot causing a problem in an actual analysis), not only the simple judgment can be carried out for the reagent whose storage condition does not satisfy a predetermined condition and the reagent whose valid period has been expired, but also by using a concrete condition which is identified by an actual utilization, it becomes possible to manage the reagent.

Furthermore, the method may further include: a step of judging, based on analysis apparatus information concerning an operation state of the analysis apparatus, whether or not the analysis apparatus is in an abnormal state. Not only the reagent, but also the analysis apparatus can be managed.

Furthermore, the method may further include: when the analysis is carried out by using the reagent in the reagent container, a step of writing data relating to a result of the analysis into the memory; and a step of storing the data relating to the result of the analysis into an analysis result data storage managed by the remote computer. Thus, by registering the data relating to the result of the analysis into not only the memory of the reagent container but also the analysis result data storage managed by the remote computer, it becomes possible to use the result of the analysis for, for example, the management of other reagents relating to this reagent.

In addition, the method may further include: when the analysis is carried out by using the reagent in the reagent container, a third step of judging, according to an abnormal detection condition for each specimen to be analyzed, whether or not there is an abnormal state, and the data relating to the result of the analysis may include information concerning the presence or absence of the abnormal state, which is judged at the third judging step.

Furthermore, the method may further include: when the analysis is carried out by using the reagent in the reagent container, a step of judging by using the data relating to the result of the analysis whether or not there is an abnormal state for the entire results of the analysis. Thus, by not only judging for each specimen whether or not there is an abnormal state, but also judging whether or not there is an abnormal state for the entire results of the analysis, it is possible to obtain more appropriate analysis result. That is, it becomes possible to support an appropriate analysis.

Moreover, the method may further include: when it is judged that there is an abnormal state for the entire results of the analysis, a step of presuming a cause of the abnormal state by using the data relating to the result of the analysis; and a step of presenting data concerning the presence or absence of the abnormal state for the entire results of the analysis and data concerning the cause of the abnormal state, which was presumed when it is judged that there is an abnormal state, for a user of the analysis apparatus. Thus, it becomes possible for the user of the analysis apparatus to carry out an appropriate measure.

An analysis apparatus according to a second aspect of this invention is an analysis apparatus that uses a reagent container having a memory to store reagent information concerning the reagent in the reagent container. The analysis apparatus has a memory reader and writer that reads and write data against the memory of the reagent container; judging means for causing the memory reader and writer to read out the reagent information concerning the reagent in the reagent container from the memory of the reagent container and judging based on the reagent information concerning the reagent in the reagent container, whether or not the reagent in the reagent container is usable; and means for transmitting at least a portion of the reagent information to a remote computer when the judging means judged that the reagent in the reagent container is usable. Then, the judging means causes the memory reader and writer to write data representing the reagent is unusable into the memory of the reagent container, when the judging means judges that the reagent in the reagent container is unusable, and causes the memory reader and writer to write data representing the reagent is unusable into the memory of the reagent container, when the data representing the reagent in the reagent container is unusable is received from the remote computer. By using such an analysis apparatus, it becomes possible to appropriately manage the reagent in the reagent container having the memory.

In addition, the analysis apparatus may further include: means for causing the memory reader and writer to write the data relating to the result of the analysis into the memory of the reagent container, when the analysis is carried by using the reagent inside of the reagent container; and means for transmitting the data relating to the result of the analysis to the remote computer. Because there is a case where the data relating to the result of the analysis is also necessary for the reagent management, it is written into the memory of the reagent container. In addition, because it is used to judge whether or not the result of the analysis is valid or the like, it is transmitted to the remote computer.

Furthermore, the analysis apparatus may further include: second judging means for judging according to an abnormal state detection condition for each specimen to be analyzed, whether or not there is an abnormal state, and the data relating to the result of the analysis may include information concerning the presence or absence of the abnormal state, which is judged by the second judging means. By judging, for the analysis, whether or not there is an abnormal state, an appropriate support for the analysis is carried out.

In addition, the data concerning the abnormal state detection condition for each specimen to be analyzed may be data updated by the remote computer. By judging by using, for example, new and more appropriate data from the remote computer, it is possible to carry out more appropriate abnormal state detection.

Furthermore, the analysis apparatus may further have: means for receiving validity data for the result of the analysis from the remote computer; and means for presenting the received validity data for the user. Then, the aforementioned second judging means may cause the memory reader and writer to write the data representing the reagent in the reagent container is usable into the memory of the reagent container, when the validity data includes data indicating the defection of the reagent.

A remote computer according to a third aspect of this invention is a remote computer cooperating with an analysis apparatus using a reagent container having a memory to store reagent information concerning the reagent in the reagent container. Then, the remote computer has judging means for judging, based on a condition as to whether or not the reagent is usable, whether or not the reagent in the reagent container is usable, when at least a portion of the reagent information is received from the analysis apparatus, wherein the condition is identified from utilization results of the reagents having a predetermined relation with the reagent in the reagent container; means for transmitting a judgment result by the judging means to the analysis apparatus when it is judged that at least the reagent in the reagent container is unusable; and means for registering data representing the reagent in the reagent container is unusable, into a reagent database, when the judging means judged that the reagent in the reagent container is unusable.

Thus, even in the remote computer, by judging from a condition derived from a plurality of utilization examples of the same type of the reagent, for example, whether or not the reagent is usable, it becomes possible to appropriately manage the reagent, and improve the business efficiency in the analysis.

Furthermore, the remote computer may further have: means for reading out latest data (e.g. option information, parameters, threshold data and the like) used in the analysis using the reagent in the reagent container from an analysis-related data storage, when the judging means judged that the reagent in the reagent container is usable, and transmitting the latest data to the analysis apparatus. It becomes possible to carry out the abnormal state detection in the analysis based on appropriate data.

Moreover, the remote computer may further have: means for storing the data relating to the result of the analysis into an analysis result data storage, when the data relating to the result of the analysis is received from the analysis apparatus; second judging means for judging by using the data relating to the result of the analysis, which is stored in the analysis result data storage, whether or not the result of the analysis has validity; and means for transmitting a judgment result by the second judging means to the analysis apparatus.

Furthermore, the aforementioned second judging means may judge by using the data relating to the result of the analysis, which is stored in the analysis result data storage, whether or not there is an abnormal state for the entire results of the analysis, and identify the presence or absence of the validity of the result of the analysis based on the presence or absence of the abnormal state for the entire results of the analysis.

In addition, the aforementioned second judging means may further carry out a processing to presume a cause of an abnormal state by using the data relating to the result of the analysis, which is stored in the analysis result data storage. By presuming the cause of the abnormal state, appropriate measures can be guided to the user.

Furthermore, the remote computer may further have means for generating data to be used for the judgment processing in at least either of the judging means and the second judging means by using a predetermined group of the data relating to the result of the analysis, which is stored in the analysis result data storage. Thus, it is possible to judge based on data suited in more actual.

In addition, the remote computer may further include: means for generating data representing the difference between the analysis apparatuses by using a predetermined group of data relating to the result of the analysis, which is stored in the analysis result data storage. By detecting the difference between the analysis apparatuses, it becomes possible to identify the necessity of the maintenance of the analysis apparatus or the like.

Furthermore, the remote computer may further include: means for predicting an occurrence of the abnormal state of the reagent or the analysis apparatus by using the data relating to the result of the analysis, which is stored in the analysis result data storage. Thus, it becomes possible to carry out appropriate measures, early.

A data analysis method according to a fourth aspect of this invention is executed by a remote computer cooperating with an analysis apparatus using a reagent container that has a memory to store reagent information concerning the reagent in the reagent container. Then, the data analysis method include: when at least a portion of the reagent information is received from the analysis apparatus, a judging step of judging, based on a condition as to whether or not the reagent is usable, whether or not the reagent in the reagent container is usable, wherein the condition is identified from utilization results of reagents having a predetermined relation with the reagent in the reagent container; when it is judged at the judging step that at least the reagent in the reagent container is unusable, transmitting a judgment result at the judging step to the analysis apparatus; and when it is judged at the judging step that the reagent in the reagent container is unusable, a step of registering data representing the reagent in the reagent container is unusable, into a reagent database.

It is possible to create a program to realize the analysis apparatus and the remote computer according to this invention. The program is stored into a storage medium or a storage device such as, for example, a flexible disk, a CD-ROM, a magneto-optical disk, a semiconductor memory, or a hard disk. In addition, the program may be distributed as digital signals over a network in some cases. Data under processing is temporarily stored in the storage device such as a computer memory.

A reagent container according to a fifth aspect of this invention has a memory that stores data used in order to cause an analysis apparatus to judge at least one of whether or not the reagent in the reagent container is usable in an analysis, and whether or not the result of the analysis using the reagent in the reagent container is appropriate, and the analysis apparatus can read out the data.

BRIEF DESCRIPTION OF THE DRAWINGS

FIG. 4-1 is a diagram showing data stored in an RF tag;

FIG. 4-2 is a diagram showing data stored in the RF tag;

FIG. 11-1 is a table showing a processing result by an inter-apparatus difference data generator;

FIG. 11-2 is a table showing a judgment reference of the processing result by the inter-apparatus difference data generator.

DETAILED DESCRIPTION OF EMBODIMENTS

Figure 1:
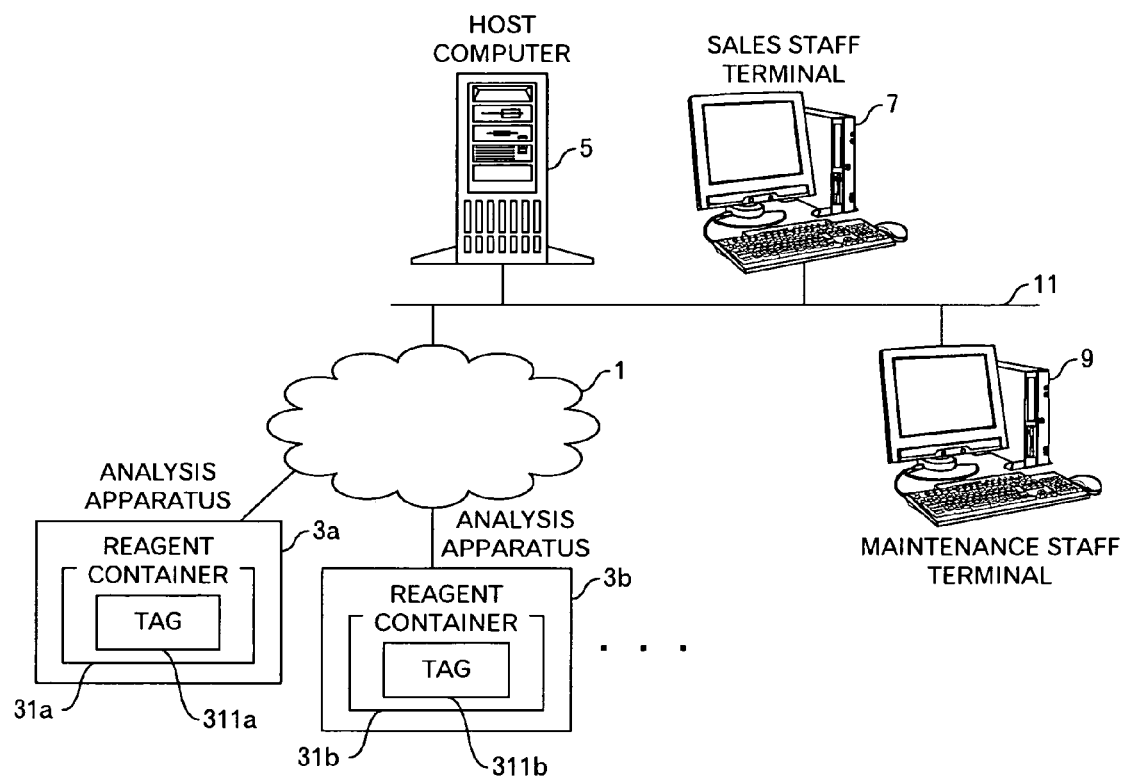
FIG. 1 is a system outline diagram in an embodiment of this invention.

FIG. 1 shows a system outline figure according to an embodiment of this invention. A network 1 that is the Internet, a dedicated communication line or the like is connected with analysis apparatuses 3a and 3b. Here, only two analysis apparatuses are shown, but the number of apparatuses is not limited to two. In addition, the network 1 is connected to a Local Area Network (LAN) 11 of a company or the like, which provides a remote monitoring service of the analysis apparatuses 3a and 3b via a communication device such as a firewall or the like, and the LAN 11 is connected to one or plural sales staff terminals 7 and one or plural maintenance staff terminals 9. The sales staff terminal 7 and the maintenance staff terminal 9 are personal computers, for example, and can access data stored in a host computer 5, and can receive mails or the like from the host computer 5.

Incidentally, hereinafter, an example is indicated in which the same company or the like carries out all of the information provision by the host computer 5, provision of insufficient reagents and maintenance service provision for the analysis apparatus, for the user of the analysis apparatus. However, there is no need to carry out all of these by the same company or the like. It is possible to change the business form to various forms such as a company or the like carrying out only the information provision or the like by the host computer 5, a company or the like carrying out only the provision of the insufficient reagents, a company or the like carrying out only the maintenance service provision for the analysis apparatus, a company or the like providing an arbitrary combination of those or the like. For example, when other company or the like carries out the provision of the insufficient reagent, the sales staff terminal 7 is not connected to the LAN 11, but is connected to another network, which is connected with the network 1, for example. In addition, when other company or the like carries out the maintenance service provision for the analysis apparatus, the maintenance staff terminal 9 is not connected to the LAN 11, but is connected to another network, which is connected with the network 1, for example.

In this embodiment, the reagent is held in a reagent container 31, and the reagent container 31 has a Radio Frequency (RF) tag 311 including a memory to store information concerning the reagent in the reagent container. It is possible to use a contact type Integrated Circuit (IC) tag, not a non-contact type IC tag such as the RF tag 311. In a reagent holder of the analysis apparatus 3, one or plural reagent containers 31 are held and used for the analysis.

Figure 2:
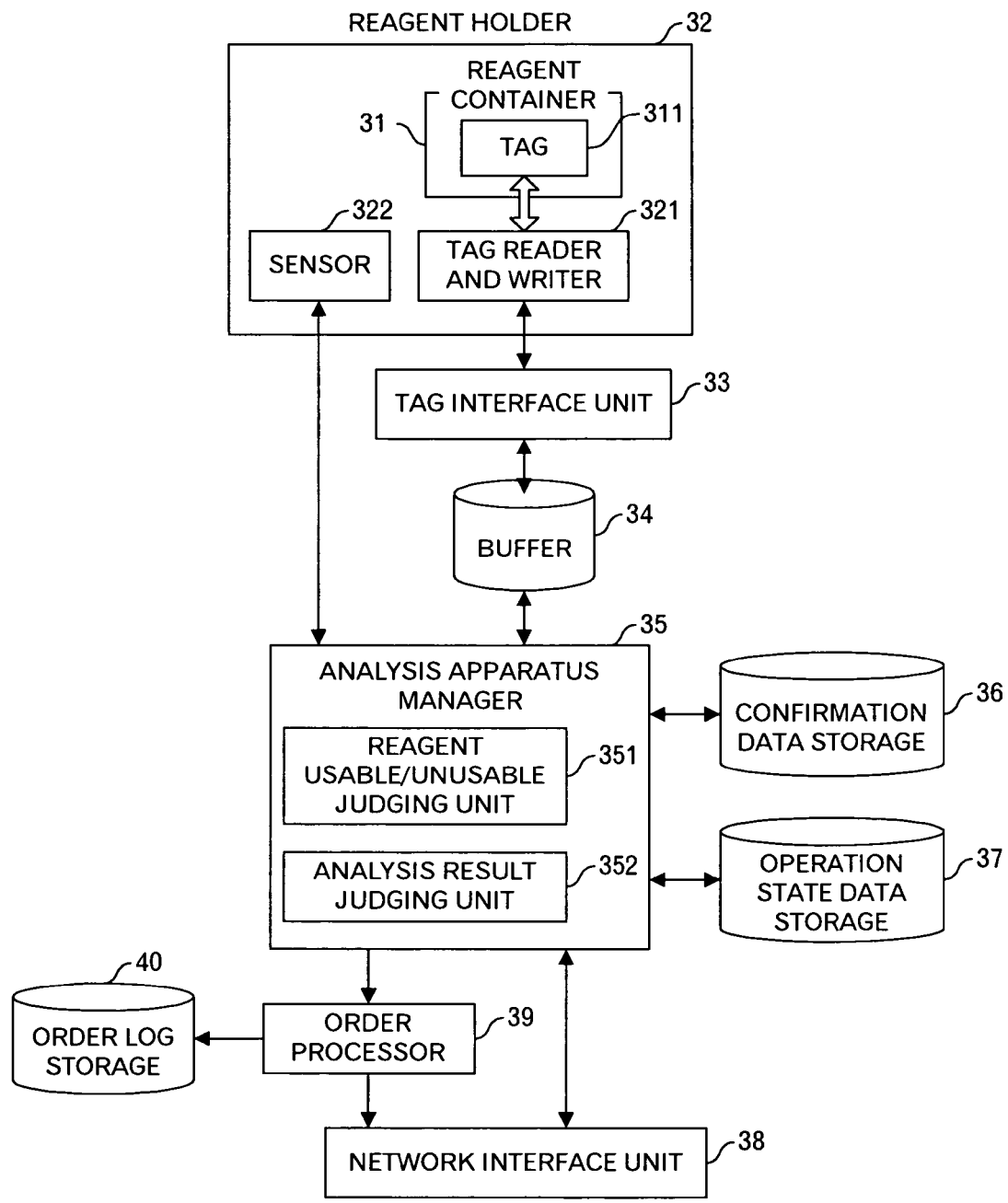
FIG. 2 is a functional block diagram of an analysis apparatus.

Next, FIG. 2 shows a functional block diagram of the analysis apparatus 3. The analysis apparatus 3 has a network interface unit 38, an order processor 39, an order log storage 40, an analysis apparatus manager 35, a confirmation data storage 36, an operation state data storage 37, a buffer 34, a tag interface unit 33, and a reagent holder 32. In addition, it may include a display device not shown. It is preferable that the reagent holder 32 has a thermal and cooling function, and the reagent holder 32 holds one or plural reagent containers 31, and has a sensor 322 to measure the temperature and humidity in the reagent holder 32, the vibration and inclination if necessary, and the like, and a tag reader and writer 321 to carry out the read/write of data against the RF tag 311 of the reagent container 31. The tag reader and writer 321 is a well-known device configured so as to conform with the RF tag 311. Therefore, further explanation is omitted. The tag reader and writer 321 reads or writes data against the RF tag 311 according to an instruction from the tag interface unit 33. Incidentally, the sensor 322 may be provided in the reagent container 31 side, and in such a case, it becomes possible to record the temperature, humidity and the like when the reagent container is left outside of the reagent holder 32 or at the transportation. In addition, a device to measure the time may be provided in the sensor 322.

The analysis apparatus manager 35 writes an instruction (including write data in a case of writing) to the tag reader and writer 321 into the buffer 34, and the tag interface unit 33 refers to the buffer 34 to carry out a processing for the tag reader and writer 321. In addition, the analysis apparatus manager 35 reads out data written into the buffer 34 by the tag interface unit 33 to carry out a processing. Moreover, the analysis apparatus manager 35 receives the measurement result from the sensor 322 in the reagent manager 32.

The analysis apparatus manager 35 has a reagent usable/unusable judging unit 351 and an analysis result judging unit 352, and refers to the confirmation data storage 36 to carry out a processing, and further causes the network interface unit 38 to transmit predetermined data to the host computer 5. In addition, when the network interface unit 38 receives data from the host computer 5, it outputs the data to the analysis apparatus manager 35. Furthermore, the analysis apparatus manager 35 stores data concerning the operation state of the analysis apparatus into the operation state data storage 37, and causes the network interface unit 38 to transmit the data to the host computer 5 at a predetermined timing (e.g. periodically, when the abnormal state is detected, or the like). Moreover, the analysis apparatus manager 35 causes the order processor 39 to carry out an order processing in response to an instruction by the user of the analysis apparatus or automatically. The order processor 39 stores order logs into the order log storage 40 for the later confirmation, for example, and generates order data, and cause the network interface unit 38 to transmit the order data to the host computer 5. The network interface unit 38 carries out a communication processing with the host computer.

The further detailed functions of these processing units will be explained in the following processing flow.

Figure 3:
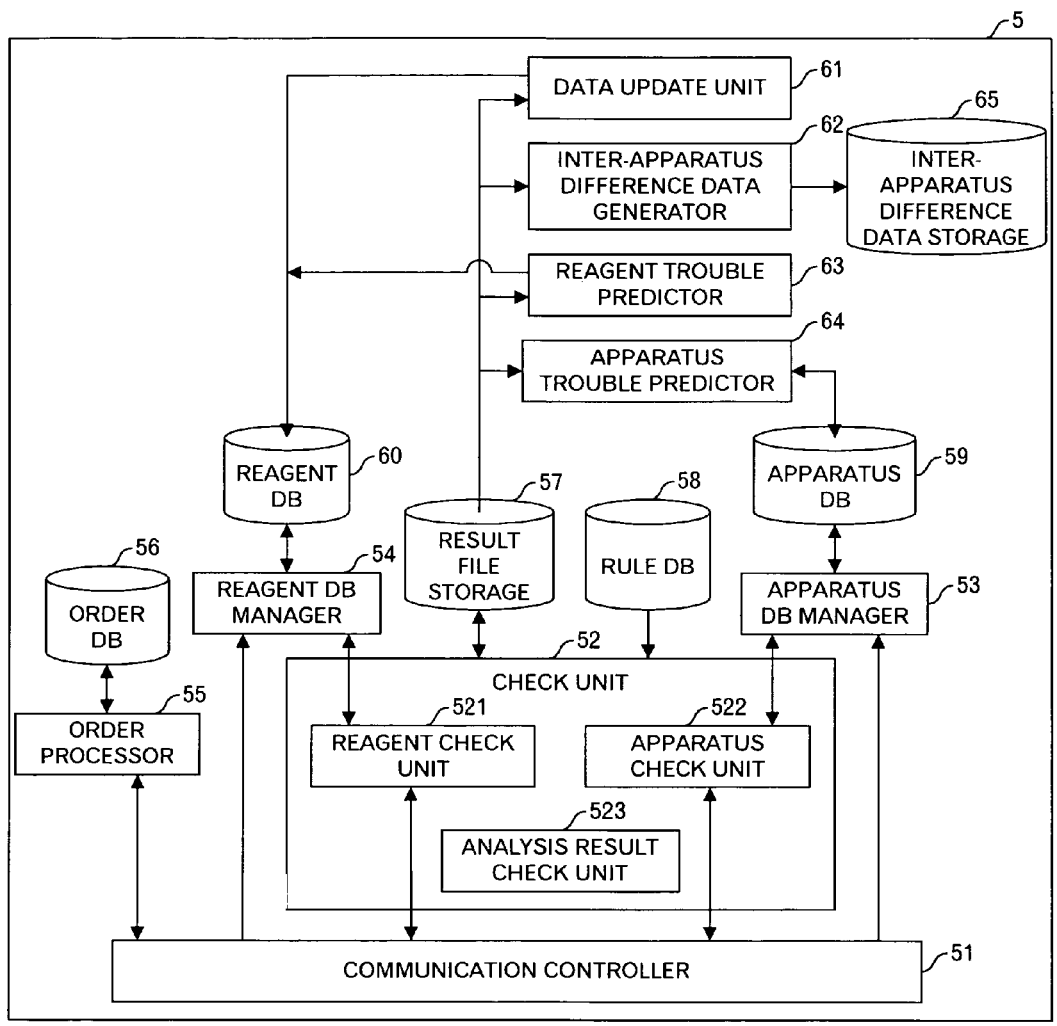
FIG. 3 is a functional block diagram of a host computer.
Figure 5:
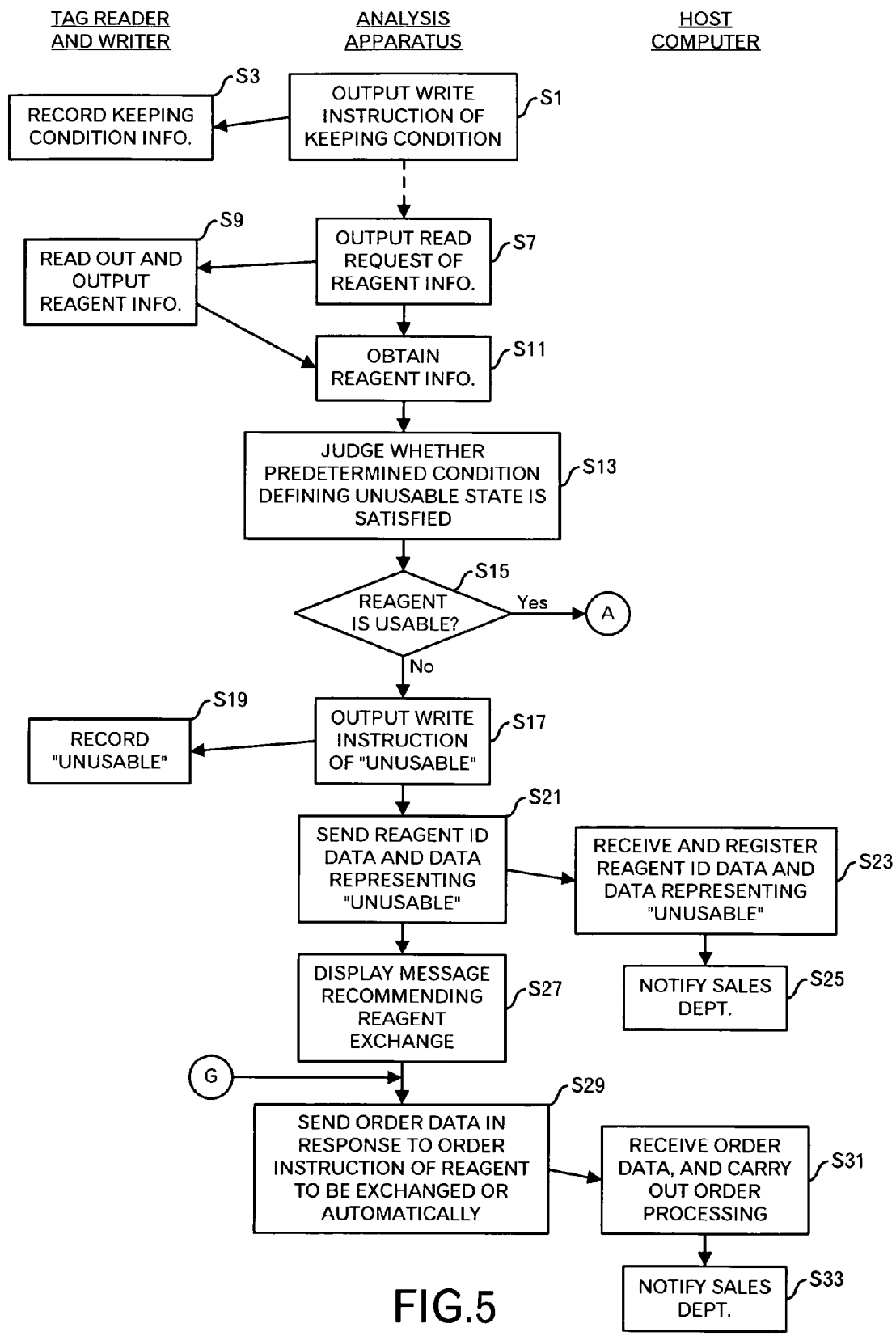
FIG. 5 is a diagram showing a first processing flow of the system.

Next, FIG. 3 shows a functional block diagram of the host computer 5. The host computer 5 has a front end unit having a communication controller 51, a check unit 52, an apparatus DB manager 53, a reagent DB manager 54, an order processor 55, an order database (DB) 56, a result file storage 57, a rule DB 58, an apparatus DB 59, and a reagent DB 60, and a back end unit having a data update unit 61, an inter-apparatus difference data generator 62, a reagent trouble predictor 63, an apparatus trouble predictor 64, and an inter-apparatus difference data storage 65.

Data from each analysis apparatus 3 is received by the communication controller 51, and is output to one of the check unit 52, the apparatus DB manager 53, the reagent DB manager 54, and the order processor 55. The check unit 52 has a reagent check unit 521, an apparatus check unit 522 and an analysis result check unit 523, and stores data into the result file storage 57 and the rule DB 58, into the reagent DB 60 via the reagent DB manager 54, into the apparatus DB 59 via the apparatus DB manager 53, and carries out a processing using the data stored in those storages. The order processor 55 stores order data of the reagent or the maintenance, which is received via the communication controller 51, into the order DB 56, and transmits a notice to the maintenance staff terminal 9 and/or sales staff terminal 7. The order processor 55 may receive the order data from the check unit 52. The reagent DB manager 54 stores data from the check unit 52 or the communication controller 51 into the reagent DB 60, and outputs data stored in the reagent DB 60 to the check unit 52 in response to a request from the check unit 52. In addition, the apparatus DB manager 53 stores data from the check unit 52 or the communication controller 51 into the apparatus DB 59, and outputs data stored in the apparatus DB 59 to the check unit 52 in response to a request from the check unit 52.

The data update unit 61 carries out an analysis processing by using data stored in the result file storage 57, and updates, for example, threshold data stored in the reagent DB 60 to the latest data. In addition, the inter-apparatus difference data generator 62 carries out an analysis processing by using data stored in the result file storage 57, compares the difference of the analysis results among the analysis apparatuses, and detects a problem occurred in the analysis apparatus by identifying the size of the inter-apparatus difference of the analysis apparatus. The processing result is stored into the inter-apparatus difference data storage 65, and if necessary, for example, an alert message is transmitted to the user of the maintenance staff terminal 9. The reagent trouble predictor 63 carries out an analysis processing by using data stored in the result file storage 57, detects a foretaste of occurrence of the reagent abnormal state, and if necessary, transmits an alert message to, for example, the user of the sales staff terminal 7. Furthermore, the apparatus trouble predictor 64 refers to the result file storage 57 and the apparatus DB 59 to carry out an analysis processing, detects a foretaste of occurrence of the apparatus trouble, and if necessary, transmits an alert message to, for example, the user of the maintenance staff terminal 9.

The further detailed functions of these processing units will be explained in the following processing flows and the like.

Next, an example of data stored in the RF tag 311 of the reagent container 31 will be indicated by using FIGS. 4-1 and 4-2. FIG. 4-1 shows information written at the shipping in addition to whether or not its update is carried out, and FIG. 4-2 shows information written after the shipping. More specifically, the information written at the shipping includes information concerning the production, information concerning the analysis conditions, information concerning the reagent capability, information concerning the display, and information concerning the result. In addition, the information written after the shipping includes information written in use and other time, and information written in use.

The information concerning the production includes the production lot number, the serial number and the expiration date. Thus, the reagent can be identified. Incidentally, here, the production lot number represents the number assigned for each production lot in a production plant when the reagent bottle (container) is produced, and the serial number represents the number assigned for each reagent bottle (container).

In addition, the information concerning the analysis conditions includes information such as parameters (specimen quantity to be consumed, reagent quantity to be consumed, measurement wavelength (main wavelength and sub-wavelength), reaction time, measurement point and the like) as conditions causing the analysis apparatus to operate in order to carry out the analysis, dilution condition (the kind of dilution solution and dilution rate) and the calibration method. Thus, it is possible to omit settings or the like by the user of the analysis apparatus, the usability is enhanced, and it is possible to improve the speed of the analysis or the like. Incidentally, the parameters are different according to the measurement items and the specimen to be analyzed. In addition, the specimen is a target object of the analysis, and indicates an object to be examined such as blood and urine, a calibrator for the calibration, and a control to confirm the calibration result. In addition, here, the calibration method is data concerning a specific operation and condition, which are indicated when the calibration is carried out. Specifically, for example, it includes a calibration type (the type of calibration curve) such as a linear expression (straight line), a quadratic, a spline curve, a Logit-log curve or the like, the number of calibrators to be measured (standard solution) (e.g. in a case of "2", two types of calibrators are used.), a concentration value of the calibrator to be measured (standard solution), the number of measurement times of the calibrator (e.g. in a case of "3", the measurement is carried out three times for one calibrator, and the measurement value is typically indicated as an average of n=3), optional information and the like. Further, the calibration is an operation to correct the measurement value using the apparatus and the reagent, and the calibrator means the specimen to correct the measurement value, and is also called standard solution. In order to confirm the correction result, it is necessary to measure the control as a specimen having the measurement value within the criterion range.

Furthermore, the information concerning the reagent capability includes information such as calibration information, the straightness, the repeatability, the influence of the coexistent material, the reaction time course, the stability, and the threshold data. Thus, the reagent capability can be identified. Incidentally, the calibration information includes a blank value at the measurement, sensitivity, calibrator concentration, the lot number of calibrator, calibration date, expiration date, calibration history, the lot number and the serial number of the used reagent and the like. Incidentally, the reaction time course includes information of the reaction process and information associated with it.

In addition, the information concerning the display includes information such as a unit, the number of display digits, the reference value (range). Thus, it is possible to omit the setting inputs or the like by the user of the analysis apparatus, and the usability is enhanced, and it is possible to improve the speed of the analysis or the like.

Furthermore, the information concerning the result includes information such as serum information, computing between items (items, computing expression, unit, and the number of digits), and the like. Thus, it is possible to omit the setting inputs or the like by the user of the analysis apparatus, and the usability is enhanced, and it is possible to improve the speed of the analysis or the like.

The aforementioned information written after the shipping includes information updated by the latest data received from the host computer 5. That is, the information item to which "Yes" is set in a column of the presence or absence of the information update in FIG. 4-1 (e.g. the information concerning the analysis condition, the information concerning the reagent capability and the like) is updated, and the information item to which "No" is set in the column (e.g. the information concerning the production and the like) is not updated.

In addition, the information written after the shipping includes information written in use and other time, and information written in use. The information written in use and other time includes information concerning the keeping condition and the like. The information concerning the keeping condition and the like includes the transportation conditions (temperature, humidity, time, vibration) and the keeping conditions (temperature, humidity, time, vibration). Here, the transportation condition indicates data concerning the temperature, humidity and vibration during the transportation of the reagent and information concerning the time required for the transportation. Moreover, the keeping condition indicates data concerning the temperature, humidity and vibration during the keeping of the reagent, and information concerning the time required for the keeping. Such information is used for the judgment of the reagent usableness/unusableness.

Furthermore, data written in use includes information concerning the utilization condition, and information concerning the result file. The information concerning the utilization condition includes the number of used times, the date of the use, the time of the use, the expiration date, remaining amount, and information of the usableness/unusableness. Thus, it is possible to obtain the information of the reagent usableness/unusableness and the capability warranty.

In addition, the information concerning the result file includes environment information, capability information and alert information. The environment information includes information such as an ID of the analysis apparatus carrying out the measurement, measurement items, measurement condition, parameters used at the measurement, information concerning an object to be measured of measured specimen, cell blank at the measurement, reaction time course at the measurement, and the analysis result. Furthermore, the capability information includes information such as the measurement blank value, information of the calibration carried out, and the control measurement result.

Next, an example of the processing flow of the system shown in FIGS. 1 to 3 will be explained by using FIGS. 5 to 11-2. First, the analysis apparatus manager 35 of the analysis apparatus 3 summarizes, as the keeping condition information, the measurement results (temperature, humidity and the like) from the time of previous writing by the sensor 322 at a timing such as periodically, immediately before the beginning of the analysis or at the abnormal state detection, and outputs the keeping condition information with a write instruction to the buffer 34 (step S1). The buffer 34 stores the keeping condition information and the write instruction data. The tag reader and writer 321 receives the keeping condition information and the write instruction, which are stored in the buffer 34, via the tag interface unit 33, and records the keeping condition information to the RF tag 311 (step S3). Because almost all the reagent used for the clinical examination includes a protein derived from a living body such as an enzyme and an antibody, a reagent easily influenced by the temperature and the like, it is necessary to manage the temperature. Therefore, in this embodiment, the analysis apparatus 3 having the reagent holder 32, which has a cooling function, is supposed, and the reagent is kept in the reagent holder 32 when the user uses the analysis apparatus. Thus, by writing the keeping condition information into the RF tag 311 of the reagent container 31, it becomes possible to confirm later whether or not the temperature, humidity and/or the like are appropriately managed in the reagent keeping. The steps S1 and S3 are carried out regardless of the following processing. Incidentally, the analysis apparatus manager 35 properly stores data or the like obtained from, for example, the sensor 322 into the operation state data storage 37, and instructs to write by using this information stored in the operation state data storage 37 at the step S1.

In addition, the analysis apparatus manager 35 of the analysis apparatus 3 outputs a read request of the reagent information to the buffer 34 before the beginning of the analysis (step S7). The buffer 34 stores the read request of the reagent information. For example, the step S7 is carried out at timing such as any selection input by the user before the beginning of the analysis, or at timing of a setting of the reagent container 31 according to circumstances. The tag reader and writer 321 receives the read request of the reagent information from the buffer 34 via the tag interface unit 33, reads out the reagent information from the RF tag 311, and outputs the reagent information to the buffer 34 via the tag interface unit 33 (step S9). The buffer 34 stores the reagent information. The analysis apparatus manager 35 obtains the reagent information stored in the buffer 34 (step S11). Here, the reagent information includes the information written at the shipping, the information concerning the keeping condition and the like, and the information concerning the utilization condition.

Next, the reagent usable/unusable judging unit 351 of the analysis apparatus manager 35 judges by using the reagent information whether or not a predetermined condition defining an unusable state is satisfied (step S13). The predetermined condition defining the unusable state includes the lack of the remaining amount, the expiration of the term of validity, the read failure of the reagent information, the reagent whose use is prohibited, and an abnormal state of the keeping temperature, humidity or both of them. In addition, an abnormal state of the vibration and/or the inclination of the reagent container may be used as the predetermined condition defining the unusable state. As for the lack of the remaining amount, it is possible to judge the remaining amount of the reagent, which is included in the reagent information. In addition, as for the expiration of the term of validity, it is also possible to judge based on the comparison of the system time and the expiration date included in the reagent information. As for the read failure of the reagent information, it is possible to judge whether or not the data output from the buffer 34 at the step S9 is data representing "the failure of the reading". As for the reagent whose use is prohibited, because the lot number and the serial number are stored in the confirmation data storage 36, it is identified by comparing such data with the lot number and the serial number included in the reagent information. Furthermore, as for the abnormal state of the keeping temperature, humidity or both of them, it is possible to confirm, based on the information concerning the keeping condition and the like, which is included in the reagent information, whether or not the reagent is kept within a predetermined temperature range or a predetermined humidity range or within a predetermined temperature range and a predetermined humidity range in the transportation and the keeping, and how long the reagent is left outside of a predetermined temperature range or a predetermined humidity range or outside of both of them. The predetermined temperature range and the predetermined humidity range are stored in the confirmation data storage 36.

Then, the reagent usable/unusable judging unit 351 judges whether or not the reagent can be used (step S15). When it is judged, based on the predetermined condition defining the unusable state, that the reagent can be used (step S15: Yes route), the processing shifts to a processing in FIG. 6 via a terminal A. When it is judged, based on the predetermined condition defining the unusable state, that the reagent cannot be used (step S15: No route), the reagent usable/unusable judging unit 351 outputs data representing the reagent cannot be used and its write instruction to the buffer 34 (step S17). The buffer 34 stores the data representing the reagent cannot be used and its write instruction. In response to this, the tag reader and writer 321 receives the data representing the reagent cannot be used and its write instruction via the tag interface unit 33, and records the data representing the reagent cannot be used (information concerning the "usable"/ "unusable". Hereinafter, it is the same.) to the RF tag 311 (step S19). However, when it is judged that the reagent cannot be used because of the read failure of the reagent information, there is a case where the writing is also impossible. Therefore, the steps S17 and S19 may be skipped.

In addition, the reagent usable/unusable judging unit 351 causes the network interface unit 38 to transmit reagent identification data (the kind of the reagent, the lot number, and the serial number) and the data representing the reagent cannot be used to the host computer 5 (step S21). When the communication controller of the host computer 5 receives the reagent identification data and the data representing the reagent cannot be used from the analysis apparatus 3, it outputs the data to the reagent DB manager 54, and causes the reagent DB manager 54 to register the data into the reagent DB 60 (step S23). Information of all the reagents, which have been shipped, and the like are registered into the reagent DB 60. That is, for the reagent of each reagent container, the information written at the shipping and a usable/unusable flag have been stored. Furthermore, shipping destination data and the like may be included. At the step S23, the reagent of a specific reagent container is identified by the reagent identification data, and the usable/unusable flag is set to "unusable" in association with it.

Furthermore, the communication controller 51 of the host computer 5 outputs the reagent identification data and the unusableness data to, for example, the order processor 55. Then, the order processor 55 does not judge the order, but transmits, as an alert message, an occurrence of a problem as to the reagent to, for example, the user of the sales staff terminal 7 (step S25). Incidentally, at this stage, it is possible to carry out an order processing, automatically.

On the other hand, the reagent usable/unusable judging unit 351 displays a message to recommend the exchange of the reagent on a display device of the analysis apparatus 3 (step S27). In addition, on a screen displaying the message to recommend the exchange of the reagent, for example, a button for the order of the reagent to be exchanged is provided, and the push of such a button is recommended to the user. Then, in response to an order instruction of the reagent to be exchanged or automatically, regardless of such an instruction according to the occasion, the order processor 39 stores an order log relating to the order of the reagent to be exchanged into the order log storage 40, and causes the network interface unit 38 to transmit order data of the reagent to be exchanged to the host computer 5 (step S29). The order data of the reagent to be exchanged includes data of the kind of the reagent and the like.

The communication controller 51 of the host computer 5 receives the order data from the analysis apparatus, and outputs the order data to the order processor 55. The order processor 55 carries out an order processing to register the order data based on the received order data into the order DB 56 (step S31). In addition, the order processor 55 notifies, for example, the user of the sales staff terminal 7 by transferring the order data (step S33). Thus, the user in charge of the sales can carry out an appropriate processing, early. In addition, based on the order DB 56, a manufacturer of the reagent can carry out the stock management and production management.

Incidentally, the predetermined unusableness condition may include a mistake of the reagent. This is detected when the reagent is not set to the reagent holder 32, the analysis to be carried out is identified, and the reagent used in the analysis is identified. However, because there is inappropriate case when the data representing the reagent cannot be used is written into the RF tag 311, only the recommendation of the exchange may be carried out when the mistake of the reagent is detected.

Figure 6:
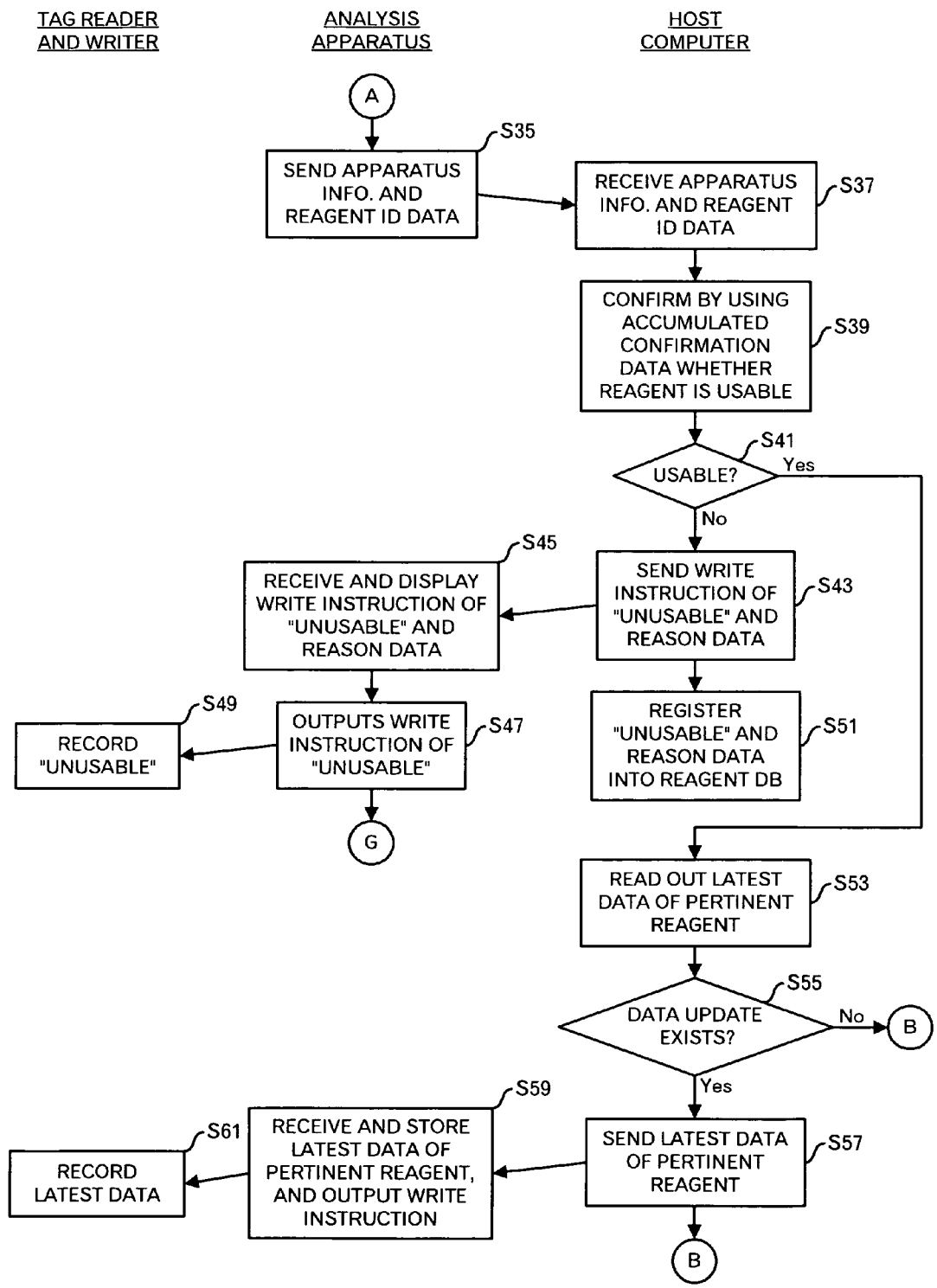
FIG. 6 is a diagram showing a second processing flow of the system.

Next, a processing subsequent to the terminal A will be explained by using FIG. 6. When the reagent usable/unusable judging unit 351 of the analysis apparatus manager 35 judged, based on the predetermined unusableness condition, that the reagent can be used, the reagent usable/unusable judging unit 351 causes the network interface unit 38 to transmit apparatus information of the analysis apparatus 3 and the reagent identification data to the host computer 5 (step S35). Here, the apparatus information includes an analysis apparatus ID and data stored in the operation state data storage 37 (measurement data by the sensor 322 and data concerning the analysis performance state) The communication controller 51 of the host computer 5 receives the apparatus information and the reagent identification data from the analysis apparatus 3 (step S37), and outputs the received data to the reagent check unit 521 and the apparatus check unit 522.

The reagent check unit 521 reads out accumulated confirmation data from the reagent DB 60 via the reagent DB manager 54, and confirms by using the accumulated confirmation data, whether or not the reagent in the reagent container, which is identified by the reagent identification data, can be used (step S39). The accumulated confirmation data includes the latest list of the lot number of the reagent container, which cannot be used, or combinations of the lot number and the serial number. Because the list of the lot numbers or combinations of the lot number and the serial number, which is held by the analysis apparatus 3, might be old, the step S39 is carried out. Incidentally, in a case of the reagent that it is understood that a large difference in the analysis result occurs between the analysis apparatuses, the lot number or the combination of the lot number and the serial number is associated with data to identify the analysis apparatus such as the analysis apparatus ID, and the set of those is registered into the list. In addition, when the reason of the unusableness is identified, the reason data is also registered. Therefore, the reagent check unit 521 checks the latest list by using the reagent identification data and the apparatus information.

Specifically, the reagent check unit 521 searches the same reagents or the reagents of the same lot number for the reagent judged to be unable to use, and confirms and judges, from the search result, whether or not there is possibility in which the reagent identified by the reagent identification data cannot be used (included in a list of the reagents judged to be unable to use). The list of the reagents judged to be unable to use can be generated by the reagent trouble predictor 63 carrying out an analysis processing by using data stored in the result file storage 57. Incidentally, it is possible to define, as an example that a specific reagent lot is judged to be unable to use, a case where the number of reagents judged to be unable to use in the reagents of the same lot number exceeds 5% of the number of all reagents of the same lot number. This list of the reagents judged to be unable to use is stored in the reagent DB 60.

When the reagent check unit 521 judges that the reagent identified by the reagent identification data cannot be used (step S41: No route), the reagent check unit 521 causes the communication controller 51 to transmit a write instruction of data representing the reagent cannot be used to the RF tag 311 and reason data to the analysis apparatus 3 (step S43). The network interface unit 38 of the analysis apparatus 3 receives the write instruction of the data representing the reagent cannot be used and the reason data from the host computer 5, and outputs the data to the analysis apparatus manager 35. The analysis apparatus manager 35 displays a message representing the reagent cannot be used and the reason data on the display device (step S45). In addition, it outputs the data representing the reagent cannot be used and its write instruction to the buffer 34 (step S47) The buffer 34 stores the data representing the reagent cannot be used and its write instruction. In response to this, the tag reader and writer 321 receives the data representing the reagent cannot be used and its write instruction via the tag interface unit 33, and records the data representing the reagent cannot be used to the RF tag 311 (step S49). The processing shifts to the step S29 via a terminal G.

In addition, the reagent check unit 521 sets "unusable" to the usable/unusable flag corresponding to the reagent identification data in the reagent DB 60, and registers the reason data into the reagent DB 60 (step S51). It is possible to carry out a processing subsequent to the step S25 hereinafter.

On the other hand, when the reagent check unit 521 judges that the reagent identified by the reagent identification data can be used (step S41: Yes route), the reagent check unit 521 refers to the reagent DB 60 via the reagent DB manager 54 to read out the latest option information, parameters and threshold data (hereinafter, these are abbreviated as the latest data.) (step S53). The option information is information necessary to use together when a specific reagent item and a reagent lot are used, and is information of the combination of the reagent lot and calibrator lot, for example. This is because there is a case where the combination of the reagent lot and the calibrator lot affects to the calibration accuracy according to the reagent item. In addition, the threshold data includes first threshold data used in the analysis apparatus 3 in the following explanation and second threshold used in the host computer 5, and here, the first threshold data is read out. The first threshold data includes a reagent blank threshold value (e.g. absorbance is less than 0.1.), a threshold value of a calibrator measurement value (e.g. absorbance is greater than 0.6 and less than 0.9.), a cell blank data threshold value, and a time course data threshold value.

The reagent check unit 521 judges whether or not data update is carried out for the data read out as the latest data (step S55). This is because there is no meaning when any update is not carried out. In addition, when the transmission history of the latest data is registered in the reagent DB 60 or the like, for example, the reagent check unit 521 judges, by referring to the reagent DB 60, whether or not there is data update, which has not been transmitted. Then, when it is judged that there is data update (step S55: Yes route), the reagent check unit 521 causes the communication controller 51 to transmit the latest data of the reagent identified by the reagent identification data to the analysis apparatus 3 (step S57). When the network interface unit 38 of the analysis apparatus 3 receives the latest data of the reagent identified by the reagent identification data from the host computer 5, the network interface unit 38 outputs the received data to the analysis apparatus manager 35. The analysis apparatus manager 35 stores the latest data of the reagent identified by the reagent identification data into the confirmation data storage 36, and outputs the latest data and its write instruction to the buffer 34 (step S59). The buffer 34 stores the latest data and its write instruction. The tag reader and writer 321 receive the latest data and the write instruction via the tag interface unit 33, and records the latest data to the RF tag 311 (step S61).

After the step S57 or when it is judged at the step S55 that there is no data update (step S55: No route), the processing shifts to a processing of FIG. 7 via a terminal B.

Figure 7:
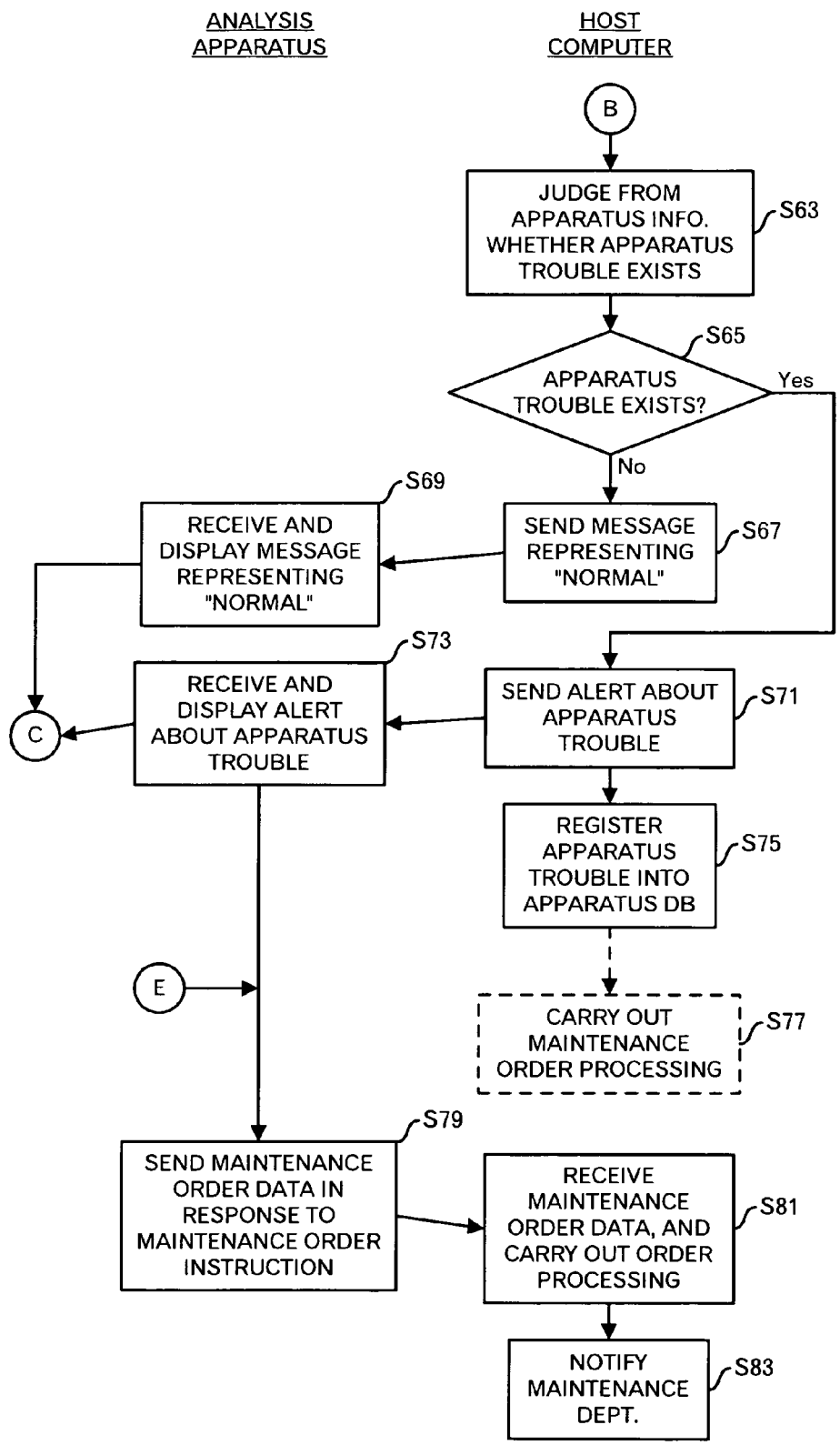
FIG. 7 is a diagram showing a third processing flow of the system.

Next, the processing subsequent to the terminal B will be explained by using FIG. 7. The apparatus check unit 522 judges from the received apparatus information whether or not there is an apparatus trouble (step S63). For example, it confirms whether or not the operation state data includes a sensor trouble, data representing other portion has any trouble, or the like. Incidentally, the judgment at the step S63 as to whether there is an apparatus trouble can be carried out at an arbitrary timing regardless of the analysis performance. When it is judged that any trouble is not found (step S65: No route), the apparatus check unit 522 generates a message representing "normal", and causes the communication controller 51 to transmit the message to the analysis apparatus 3 (step S67). When the network interface unit 38 of the analysis apparatus 3 receives the message representing "normal" from the host computer 5, the network interface unit 38 outputs the message to the analysis apparatus manager 35. The analysis apparatus manager 35 displays the message representing "normal" on the display device (step S69). Then, the processing shifts to a processing of FIG. 8 via a terminal C.

On the other hand, when it is judged that there is an abnormal state (step S65: Yes route), the apparatus check unit 522 generates an alert message about the apparatus trouble and causes the communication controller 51 to transmit the message to the analysis apparatus 3 (step S71). The network interface unit 38 of the analysis apparatus 3 receives the alert message about the apparatus trouble from the host computer 5, and outputs the message to the analysis apparatus manager 35. The analysis apparatus manager 35 displays the alert message about the apparatus trouble on the display device (step S73). The user of the analysis apparatus watches the alert message, and may carry out appropriate measures in order to solve the apparatus trouble to start the analysis (in a case where the processing shifts to a processing of FIG. 8 via a terminal C); or may push a maintenance order button also provided on the display screen of the alert message to input a maintenance order instruction. When the analysis apparatus manager 35 of the analysis apparatus 3 accepts the maintenance order instruction from the user, the analysis apparatus manager 35 generates maintenance order data specifying the abnormal portion, and stores the maintenance order data into the order log storage 40 and causes the network interface unit 38 to transmit the maintenance order data to the host computer 5 (step S79). The communication controller 51 of the host computer receives the maintenance order data from the analysis apparatus 3, and outputs it to the order processor 55. The order processor 55 carries out an order processing such as registering the received maintenance order data into the order DB 56 (step S81) For example, the maintenance order data is transferred to the user of the maintenance staff terminal 9 to notify that the maintenance order is carried out (step S83).

Incidentally, after the step S71, the apparatus check unit 522 registers data representing the apparatus trouble into the apparatus DB 59 (step S75). The apparatus DB 59 stores an analysis apparatus ID, a state flag representing "normal" or "abnormal", operation state data, date and reason data when an occurrence of the abnormal state is detected, and the like. At the step S75, the state flag is set so as to represent the abnormal state, and the reason data (the data of the reason why it is judged to be abnormal) is registered with the date data. In addition, in such a case, it is possible to automatically transmit the maintenance order data from the apparatus check unit 522 to the order processor 55. Also in such a case, the order processor 55 carries out a maintenance order processing, similarly to a processing for the maintenance order data from the analysis apparatus 3 (step S77). In addition, it is possible to notify the user of the maintenance staff terminal 9 of the occurrence of the apparatus trouble.

Figure 8:
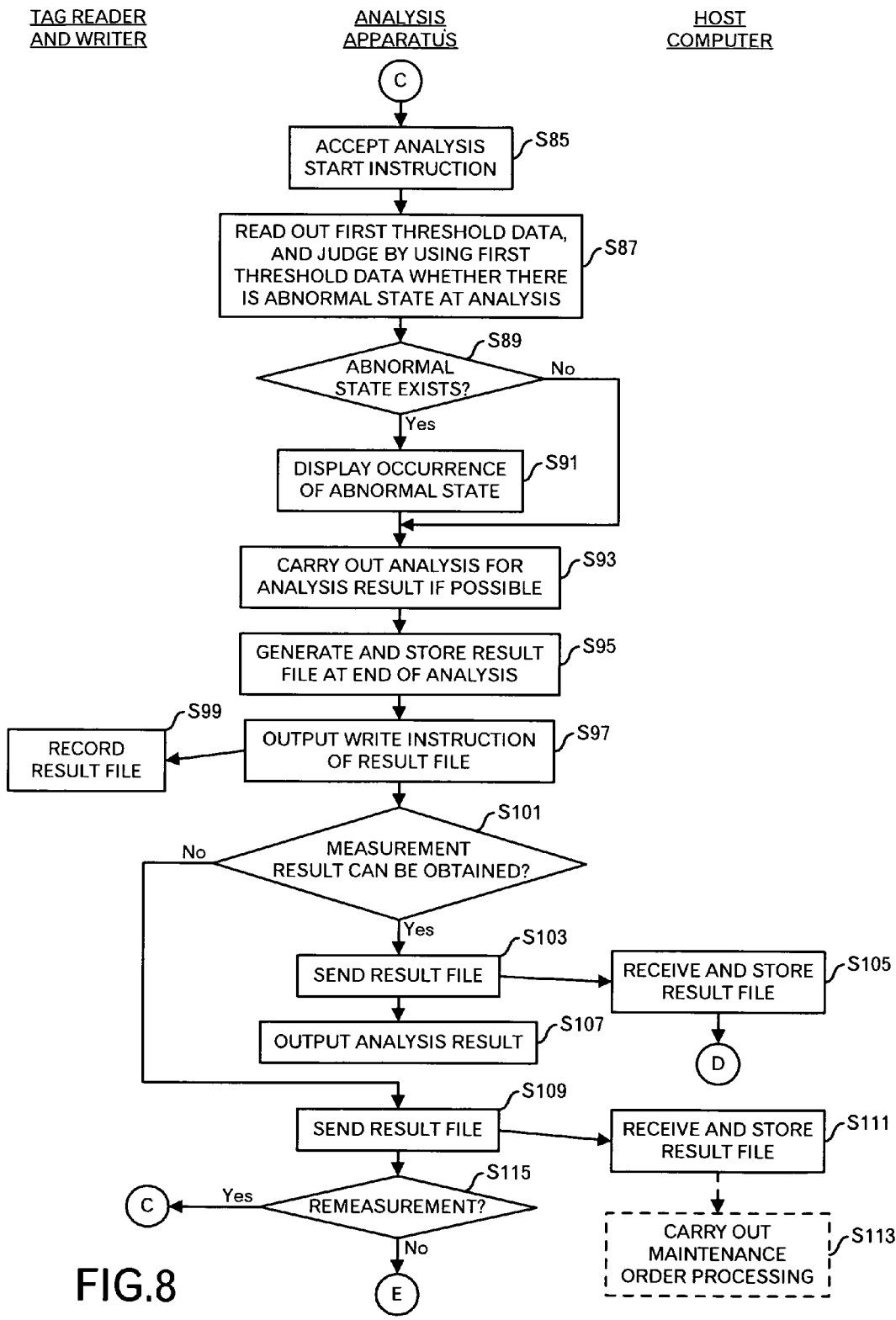
FIG. 8 is a diagram showing a fourth processing flow of the system.

The processing subsequent to the terminal C will be explained by using FIG. 8. For example, the user of the analysis apparatus 3 sets specimens to be analyzed to the analysis apparatus 3 and instructs to start an analysis. The analysis apparatus manager 35 of the analysis apparatus 3 accepts an analysis start instruction from the user (step S85). Then, the analysis apparatus manager 35 starts the analysis using the reagent information stored in the confirmation data storage 36 and the reagent itself. In addition, the analysis result judging unit 352 reads out the first threshold data from the confirmation data storage 36, and judges, by using the first threshold data, whether or not there is an abnormal state at the analysis (step S87). At the step S87, the presence or absence of the abnormal state at the analysis is judged for each specimen. Incidentally, there is case where the latest first threshold data is not received from the host computer 5 at the step S57. Therefore, in such a case, the first threshold data included in the reagent information read out from the RF tag 311 is used. The specific judging method is as follows: for example, when the threshold of the equilibrium arrival time of the reaction time course is defined as "within 5 minutes" after the beginning of the reaction for the time course in a specific measurement item, it is judged that there is an abnormal state at the analysis in a case where the measured equilibrium arrival time of the reaction time course is 6 minutes.

When the abnormal state is detected by the judgment (step S89: Yes route), the analysis apparatus manager 35 displays the occurrence of the abnormal state on the display device to notify the user (step S91). The step S91 is carried out for each detection of the occurrence of the abnormal state. When the abnormal state is not detected by the judgment (step S89: No route), or after the step S91 if possible even if there is an abnormal state, the analysis apparatus manager 35 analyzes the analysis result (step S93). Because this is a normal processing in the analysis apparatus, the further explanation is omitted. Then, the analysis apparatus generates a result file at the end of the analysis, and stores it into, for example, the buffer 34 (step S95). In addition, the content (there is also a case of a portion) of the result file is displayed on the display device of the analysis apparatus 3. In this embodiment, in any cases, that is, in a case where the abnormal state is not detected at the analysis and the measurement is normally completed, in a case where the abnormal state is detected at the analysis but the measurement itself is completed, in a case where the abnormal state is detected at the analysis and the measurement result cannot also be obtained but the analysis is ended (including a case where the analysis apparatus 3 automatically terminates the analysis and a case where the user stops the analysis in response to the display of the occurrence of the abnormal state) and the like, it is said that the analysis is ended. The result file includes the environment information and the capability information, and alert information when the abnormal state is detected. As described also in FIG. 4-2, the environment information includes an analysis apparatus ID, measurement items, measurement conditions, parameters used at this time, specimen information of the specimen measured at this time, cell blank at this time (absorbance for only the cell (reaction and detection container of the reagent) used at the measurement. it represents the degree of the infection of the cell.), time course information at this time and the analysis result (actually measured value information). Here, the specimen information includes an ID of the specimen, a kind (blood, urine or the like), examination result such as color (distinction of hemolysis, chyle, bilirubin specimen or the like), viscosity and the like and information associated with them. In addition, the actually measured value information includes an actually measured value of the specimen before the calibration, a measurement value after the calibration, and information concerning the comparison result with a reference value (range). As described also in FIG. 4-2, the capability information includes a measurement blank value at this time, calibration information carried out at this time, and a control measurement result at this time. The alert information includes information concerning a user's operation mistake, an abnormal state of the reagent, a trouble of the analysis apparatus, and an abnormal state of the result, and information to judge those (e.g. threshold data or the like).

Then, the analysis result judging unit 352 outputs the result file and its write instruction to the buffer 34 (step S97). The buffer 34 stores the result file and its write instruction. The tag reader and writer 321 receive the result file and its write instruction through the tag interface unit 33, and records the result file into the RF tag 311 (step S99).

Then, when the measurement result could be obtained in the analysis carried out above regardless of the presence or absence of the abnormal state (step S101: Yes route), the analysis result judging unit 352 causes the network interface unit 38 to transmit the result file to the host computer 5 in order to judge the validity of the analysis result or the like (step S103). The communication controller 51 of the host computer 5 receives the result file from the analysis apparatus 3, and outputs the result file to the analysis result check unit 523 of the check unit 52. The analysis result check unit 523 stores the result file into the result file storage 57 (step S105). In addition, the analysis result judging unit 352 displays the analysis result on the display device (step S107). The processing after this shifts to a processing of FIG. 9 via a terminal D.

On the other hand, when the measurement result cannot be obtained in the analysis carried out above (step S101: No route), the analysis result judging unit 352 causes the network interface unit 38 to transmit the result file only for the report of the analysis result because the judgment of the validity by the analysis result check unit 523 is useless in the state where the measurement result cannot be obtained (step S109). The communication controller 51 of the host computer 5 receives the result file from the analysis apparatus 3, and stores the result file into the result file storage 57 through the check unit 52 when the actually measured value information indicates vacant (e.g. Null) (step S111). Incidentally, in such a case, the alert information is also attached. Therefore, when the alert information includes data representing the trouble of the analysis apparatus 3, the communication controller 51 may output the result file to the order processor 55, and the order processor 55 may automatically carry out the maintenance order processing for the analysis apparatus 3 of the transmission source of the result file (step S113).

Then, when the measurement is carried out again (step S115: Yes route), the processing returns to the step S85, and when the measurement is not carried out again (step S115: No route), the processing shifts to the step S79 of FIG. 7 via a terminal E.

Incidentally, when a minor abnormal state defined in a list stored in, for example, the confirmation data storage 36 is detected, the user is prompted to remove the cause of the abnormal state. This is because the speedy analysis becomes possible when the measurement is carried out again, and the processing shifts to the No route at the step S101. Here, the minor abnormal state means an abnormal state caused by the user's mis operation or the like, and includes apparatus troubles whose cause can be easily removed by the user, such as utilization of the incorrect sample or reagent, abnormal measurement value because of the lack of the sample volume or the like, unnecessary object caught by the apparatus.

Figure 9:
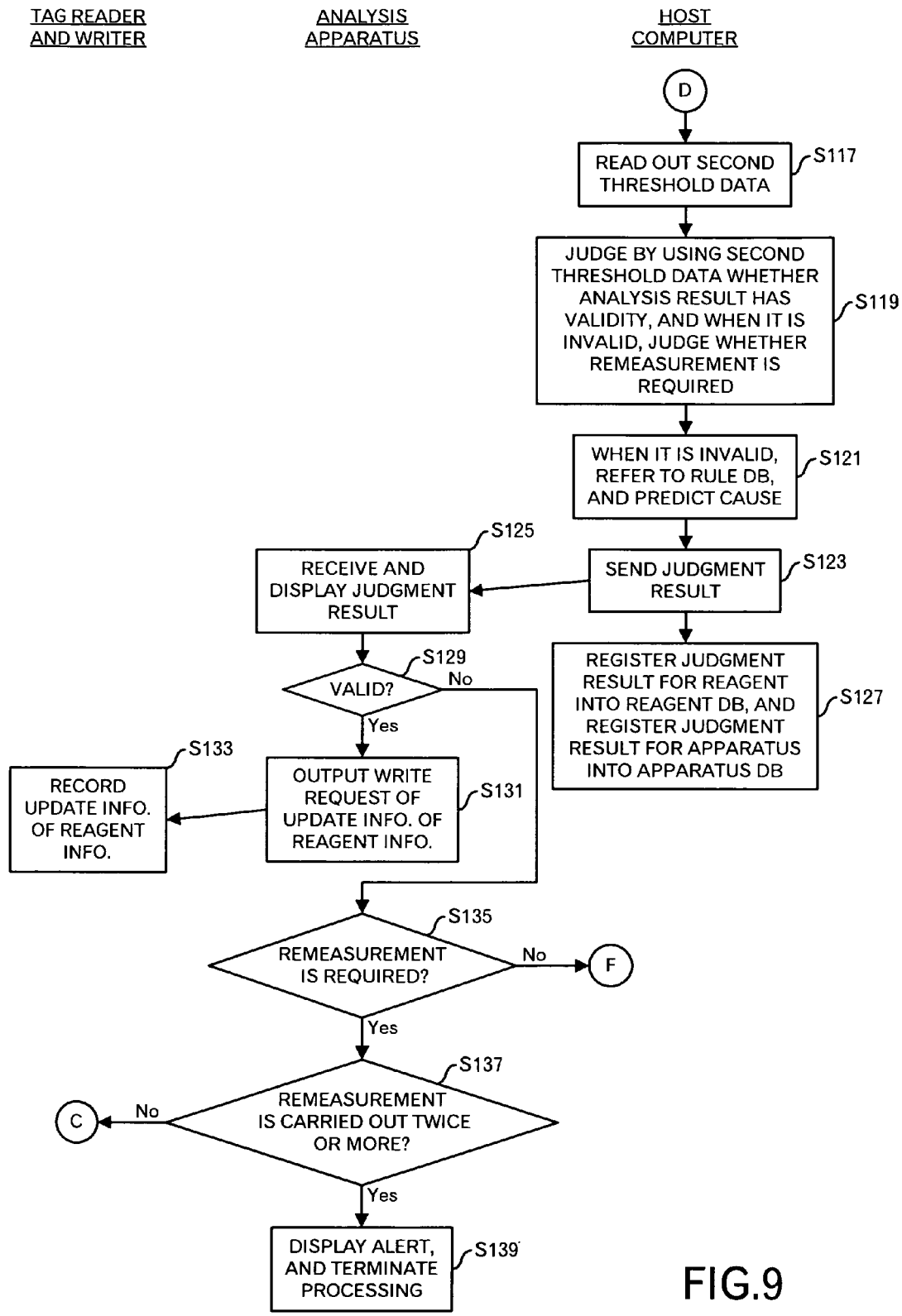
FIG. 9 is a diagram showing a fifth processing flow of the system.

Next, the processing subsequent to the terminal D will be explained by using FIG. 9. The analysis result check unit 523 reads out the second threshold data stored in the reagent DB 60 through the reagent DB manager 54 (step S117). The second threshold data is data to judge the presence or absence of the entire validity of the analysis results. More specifically, it includes a reagent blank threshold value, a threshold value for the calibrator measurement value, a threshold value for the control measurement value, specimen information, a cell blank data threshold value, a time course threshold value, a time course data threshold value and the like. Then, the analysis result check unit 523 judges the presence or absence of the validity of the analysis result by using the second threshold data and further by using data stored in the result file storage 56 if necessary, and judges whether or not the measurement should be carried out again when there is no validity (step S119). Here, the validity of the entire analysis result is basically judged, and the judgment that cannot be carried out in individual analysis apparatuses 3 is carried out in the host computer 5 side.

At the step S119, the validity of the analysis result is judged in association with the reagent blank threshold value by comparing a value at the beginning of the measurement with a value at the end of the measurement, checking aging, comparing with measurement data of another reagent having the same lot number as that of the used reagent (e.g. aging check of the reagent blank or the like), comparing with data for other analysis apparatuses, or the like. In addition, the validity of the analysis result is judged in association with the threshold value for the calibration measurement value by comparing with the previous analysis, checking the aging, comparing with other calibrator lots (check for the aging or the like), comparing the measurement data of the used reagent with the measurement data of other reagents having the same lot number (e.g. aging check of the calibrator measurement values or the like), comparing with data for other analysis apparatuses or the like. Furthermore, the validity of the analysis result is judged in association with the threshold value for the control measurement value by comparing with the threshold value for the actually measured value before the calibration, comparing with the threshold value for the measured value after the calibration, comparing with a value of the previous time for the control specimen, checking the aging, comparing with the measurement data of the used reagent with the measurement data of other reagents having the same lot number (e.g. aging check of the calibrator measurement values or the like), comparing with data of other control lots (check of the aging or the like), comparing with data for other analysis apparatuses or the like. In addition, the validity of the analysis result is judged in association with the threshold value for the cell blank data by checking the aging, comparing with data for other analysis apparatuses or the like. Furthermore, the validity of the analysis result is judged in association with the threshold value for the time course data by comparing with a value of the previous time, checking the aging, comparing with data for other analysis apparatuses, or the like. Thus, necessary result files other than the result file at this time is also read out from the result file storage 57 to use them in this processing.

The specific method of the judgment carried out at the step S119 is as follows: in a case where an example of the judgment by, for example, the reagent blank data is picked up, for example, a reagent wherein the average reagent blank increased value of the reagent in the same reagent lot used in the analysis is a data value "5" for one week, and its upper limit of the threshold is a data value "10" is picked up. In this case, when the blank increased value of the reagent currently used is a data value "12" for one week, which was obtained from the analysis result, the analysis result to be judged for the reagent blank data is judged as being invalid. Similarly, the validity can be respectively judged for other data associated with the reagent blank by using their threshold values.

Furthermore, plural threshold values may be defined. That is, there is a case where a threshold value to define a warning level and a threshold to define a level representing invalidity are provided. For example, when a value is greater than (or less than) the threshold value to define the level representing the invalidity, it is directly judged as being invalid, and when a value is greater than (or less than) the threshold value to define the warning level, the final validity is judged by a combination with other judgment results, the number of detection times of the warning level or the like. Incidentally, it is possible to define three or more threshold values, and various modes can be adopted in such a case. For example, points are defined according to the serious degree of the warning level, and when the sum of the points according to the detected warning levels or the like becomes greater than a predetermined value, it is judged as being invalid.

Incidentally, as for the necessity of the remeasurement, there is a case where it is statistically judged that the remeasurement is proper. Therefore, it is judged whether or not such a case is applicable.

In addition, the analysis result check unit 523 refers to the rule DB 58 when it is judged as being invalid at the step S119, and presumes its cause (step S121). Incidentally, when it is judged as being valid at the step S119, because there is no need to presume the cause, the step S121 is not carried out. Although there are various methods for this processing, the following processing is carried out, for example. That is, the cause for the analysis result (or measurement result) of the individual specimen is presumed by using, for example, rule data stored in the rule DB 58, and the causes are aggregated for the analysis results of all the specimens. Here, based on the cause appeared most frequently, the cause is presumed for the reagent or the analysis apparatus by using, for example, other rule data stored in the rule DB 58. It is also possible to identify the cause by applying the rule data obtained from the past actual results, which is stored in the rule DB 58, according to not only the causes appeared most frequently but also an appearance rate or the combination.

Then, the analysis result check unit 523 causes the communication controller 51 to transmit the judgment result at the steps S119 and S121 to the analysis apparatus 3 (step S123). The judgment result is stored in the result file storage 57 in association with the result file. When it is judged that there is no validity, the analysis result check unit 523 sets "unusable" to the usable/unusable flag of the reagent in the reagent DB 60 when the cause is the reagent, or sets "abnormal" to the state flag for the analysis apparatus in the apparatus DB 59 when the cause is the analysis apparatus (step S127). The date and the reason data are also registered in the apparatus DB 59. The reason data may be registered also in the reagent DB 60.

The network interface unit 38 of the analysis apparatus 3 receives the judgment result data from the host computer 5, and outputs the data to the analysis result judging unit 352 of the analysis apparatus manager 35 (step S125). The analysis result judging unit 352 displays the received judgment result data on the display device of the analysis apparatus 3 (step S125), and judges whether or not the judgment representing "valid" was obtained (step S129). When the judgment representing "valid" was obtained, the analysis result judging unit 352 outputs update information of the reagent information and its write instruction to the buffer 34 (step S131). The buffer 34 stores the update information of the reagent information and its write instruction. The update information of the reagent information includes the residual quantity of the reagent and the like. However, the validity judgment result for the analysis result file at this time may also be written at this step. The tag reader and writer 321 record the update information of the reagent information, which was received from the tag interface unit 33 (step S133).

On the other hand, when it is judged that there is no validity, it confirms whether or not it is judged that the remeasurement is required (step S135). When it is judged that the remeasurement is required, it judges whether or not the remeasurement was carried out twice or more (step S137). When the remeasurement was carried out only once, the processing returns to the step S85 of FIG. 8 through the terminal C. Incidentally, before shifting to the step S85, for example, a counter to count the number of remeasurement times is incremented by "1". But then, when the remeasurement was carried out twice or more, it may carry out an alert display on the display device of the analysis apparatus 3, and may terminate the processing (step S139). On the other hand, when it is judged that the remeasurement is not required, the processing shifts to a processing of FIG. 10 via a terminal F.

Figure 10:
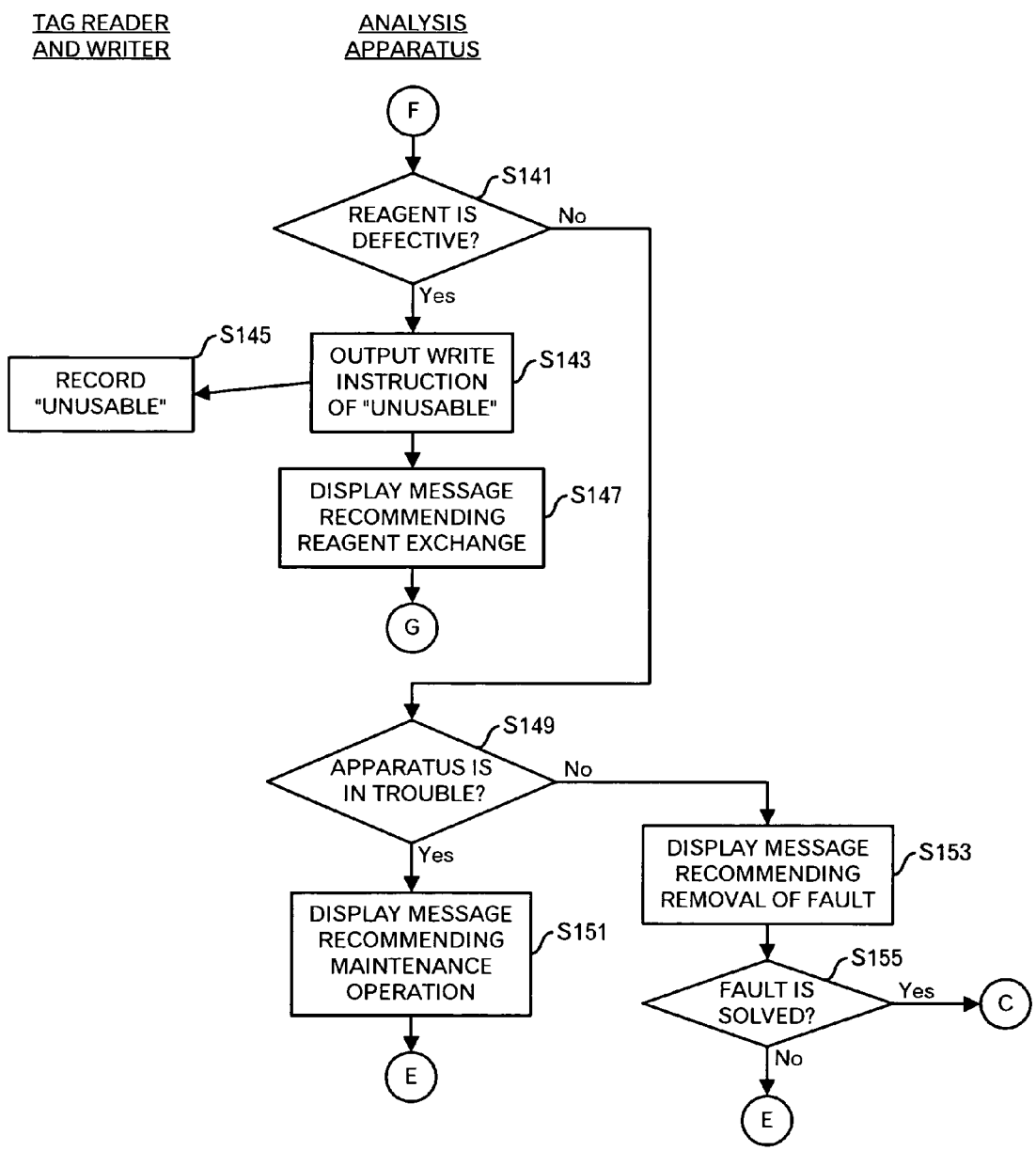
FIG. 10 is a diagram showing a sixth processing flow of the system.

The processing subsequent to the terminal F will be explained by using FIG. 10. The analysis result judging unit 352 confirms whether or not the judgment result includes the reagent defectiveness as the cause (step S141). When the reagent defectiveness is presumed as the cause, it outputs data representing it is unusable and its write instruction to the buffer 34 (step S143). The buffer 34 stores the data representing it is unusable and its write instruction. The tag reader and writer 321 accepts the data representing it is unusable and its write instruction from the buffer 34 through the tag interface unit 33, and records the data representing it is unusable into the RF tag 311 (step S145). In addition, the analysis result judging unit 352 displays a message recommending the exchange of the reagent on the display device of the analysis apparatus 3 (step S147). After this, the processing shifts to the step S29 of FIG. 5 through a terminal G.

On the other hand, when the cause is not the reagent defectiveness, the analysis result judging unit 352 confirms whether or not the judgment result includes the trouble of the analysis apparatus 3 as the cause (step S149). When the trouble of the analysis apparatus 3 is presumed as the cause, it displays a message recommending the maintenance operation on the display device (step S151). Then, the processing shifts to the step S79 of FIG. 7 through the terminal E.

Furthermore, when the cause is not the trouble of the analysis apparatus 3, the analysis result judging unit 352 displays a message recommending the removal of the fault on the display device of the analysis apparatus 3 (step S153). The fault includes the defectiveness of the calibrator, the abnormal state of the specimen or the like. In response to this, the user carries out any measures, and when the fault is solved (step S155: Yes route), the processing shifts to the step S85 through the terminal C. On the other hand, when the fault is not solved (step S155: No route), the processing shifts to the step S79 through the terminal E.

By carrying out such a processing, the management of the reagent and the validity judgment of the analysis are automatically carried out, and the business efficiency of the user of the analysis apparatus 3 is enhanced. In addition, because it becomes possible to order the reagent and the maintenance, the total analysis support becomes possible. Although the processing contents of the analysis apparatus 3 and the front end of the host computer 5 were described above, the processing of the back end of the host computer 5 is also important in this embodiment. The back end processing includes a processing by the data update unit 61, the inter-apparatus difference data generator 62, the reagent trouble predictor 63 and the apparatus trouble predictor 64.

The data update unit 61 updates the first and second threshold data by using the data stored in the result file storage 57, and stores data into the reagent DB 60. For example, as to the threshold value for the control measurement value, the data update unit 61 extracts data to be processed from the result file storage 57 under a condition such as the same reagent lot, in a period for which data is measured, excluding data judged to be abnormal or the like. Then, it carries out a predetermined statistical processing to determine the new threshold data. For example, when the threshold is determined as from (average value−3×standard deviation) to (average value+3×standard deviation), it calculates the average value and the standard deviation from the extracted data, and calculates the threshold according to the aforementioned expression. The new threshold data as the calculation result is stored in the reagent DB 60. This calculation is carried out at an arbitrary timing, and when it is registered into the reagent DB 60, the first threshold value is transmitted to the analysis apparatus 3, and the second threshold is used in the analysis result check unit 523 for each analysis. Therefore, the judgment is carried out by using the latest data. Incidentally, the processing method, judgment method, reference and the like in the data update unit 61 may be different according to the data to be updated, measured items or the like.

In addition, the inter-apparatus difference data generator 62 is a function for the quality management among the analysis apparatuses, and refers to the result file storage 57 to carry out a processing. For example, a processing content will be explained as a case when a difference between the analysis apparatuses is checked by using the control measurement result included in the calibration information. For example, it extracts the control measurement results from the result file storage 57 under predetermined conditions set for the measurement day, the measurement item, the reagent lot, the control lot and the like. Then, it carries out a predetermined statistical processing (e.g. calculation of an absolute value of the difference with the average value), and judges, for each analysis apparatus, by the result (the absolute value of the difference) of the statistical processing. For example, as shown in FIG. 11-1, a data value is identified in association with the apparatus ID, and after the average value is calculated, "|data value−average value|" is calculated. The judgment is carried out according to a reference table as shown in FIG. 11-2. In an example of FIG. 11-2, in a case of a value less than 10, there is no difference between the apparatuses, in a case of a value equal to or greater than 10 and less than 20, there is no difference between the apparatuses (however, monitor is required), in a case of a value equal to or greater than 20 and less than 30, an attention is required, in a case of a value equal to or greater than 30 and less than 40, the difference between the apparatuses is detected, and in a case of a value equal to or greater than 40, a large difference between the apparatuses is detected. This judgment result is stored in the inter-apparatus difference data storage 65. Then, the judgment result may be transmitted to the analysis apparatus 3 to notify the user of the analysis apparatus 3 of the judgment result. In addition, for example, as for the analysis apparatus 3 judged that the difference between the apparatuses is large, an alert message may be transmitted to the user of the maintenance staff terminal 9. Furthermore, it is also possible to formally cause the order processor 55 to carry out the maintenance order processing.

In addition, the reagent trouble predictor 63 uses the data stored in the result file storage 57 to carry out a processing such as judging the tendency such as increase of the judgment of the invalidity and the detection of the abnormal state in a specific reagent lot to predict an occurrence of the reagent abnormal state. As a result, when the occurrence of the reagent abnormal state is predicted in probability equal to or greater than a predetermine reference, the reagent lot number is registered in the reagent list for the unusable reagents in the reagent DB 60, for example.

Furthermore, the apparatus trouble predictor 64 uses the data stored in the result file storage 57 and the apparatus DB 59 to carry out a processing such as judging the tendency such as an increase of the detection of the abnormal state in a specific type of the analysis apparatuses to predict the occurrence of the analysis apparatus trouble. As a result, for example, an alert of the trouble occurrence is registered, for example, in the apparatus DB 59, the analysis apparatus 3 is caused to transmit an alert message, the alert message is transmitted to the user of the maintenance staff terminal 9, and the order processor 55 is actually caused to automatically carry out the maintenance order processing.

By constructing and using a system as described above, the following effects are obtained. That is, the reagent trouble predictor 63 and the apparatus trouble predictor 64, which use the data stored in the result file storage 57, are provided, and it is possible to predict the abnormal state before it occurs for a specific reagent lot or serial number, or it is possible to predict the trouble before it occurs in a specific analysis apparatus, and it becomes possible to deal with any problems before it occurs. In addition, it is possible to predict the life of the reagent and the life of the analysis apparatus and it is possible to enhance the reliability of the entire analysis system. Moreover, the production management and the stock management become easy. Furthermore, because the user of the analysis apparatus 3 can deal with the abnormal state before it occurs, the decrease of the complaint rate is expected.

In addition, the inter-apparatus difference data generator 62, which uses the data stored in the result file storage 57, is provided, and it becomes possible to collect data of the difference between the analysis apparatuses. Therefore, measures to decrease the difference between the analysis apparatuses can be performed at any time, and the accuracy of the data can be improved.

Furthermore, because the result file storage 57 and the apparatus DB 59 are managed, it becomes possible to easily identify the trouble of the analysis apparatus and the cause by using data from plural analysis apparatuses.

In addition, although it is not shown in FIG. 3, complaint information is also stored in the host computer 5. Then, it becomes possible to output a prior measure method from the correlation with the troubles of the reagent and the analysis apparatus. That is, by analyzing the state of the analysis apparatus and the reagent before the complaint occurs, it becomes possible to change the rule of the trouble prediction to more appropriate one.

Furthermore, because the order data is stored in the order DB 56 by the order processor 55, it is possible to carry out the production management and the stock management by using this data. Moreover, by analyzing the data stored in the order DB 56, the tendency of the utilization state of the user and the tendency of the maintenance of the analysis apparatus are identified. Then, it becomes possible to obtain useful information for the reagent manufacturer and the analysis apparatus manufacturer such as prediction of the part exchange timing, prediction of the reagent delivery timing, extraction of the improved points of the analysis apparatus and the like.

In addition, because it is possible to write data into the RF tag 311 of the reagent container 31 from the remote host computer 5, the latest data concerning the reagent can be written. Then, the analysis accuracy is improved. Moreover, by writing data representing "unusable" to the unusable reagent, it is possible to avoid a situation that the analysis is mistakenly carried out by using the unusable reagent. Thus, the analysis efficiency can be enhanced, and the reduction of the cost and workload is realized. In addition, because the unusable state for a specific reagent is notified to the host computer 5, the collection can be rapidly carried out.

Although one embodiment of this invention was described above, this invention is not limited to this. For example, the host computer 5 can realize the aforementioned functions by plural computers, not by one computer. In addition, it is possible to change the functional division between the analysis apparatus 3 and the host computer 5 to a certain extent. For example, it is possible to carry out the judgment as to whether or not the reagent before the analysis can be used, entirely by the host computer 5, and it is also possible that the necessary latest data is transmitted to the analysis apparatus 3, and the analysis apparatus 3 totally judges to transmit the judgment result to the host computer 5. Similarly, it is possible to carry out the judgment of the analysis result after the analysis entirely by the host computer 5, and it is also possible that necessary data is transmitted to the analysis apparatus 3, and the analysis apparatus 3 carries out all processings to transmit the analysis result to the host computer 5.

In addition, although an example that only the RF tag 311 is provided for the reagent container 31 is indicated, a sensor such as a temperature sensor may further be provided for the reagent container 31. In such a case, a variation that the trouble of the sensor 322 is detected can be adopted when a difference between a temperature by the sensor of the reagent container 31 and a temperature by the sensor 322 is equal to or greater than the tolerance. Other functions may be further added to the reagent container 31.

Figure 12:
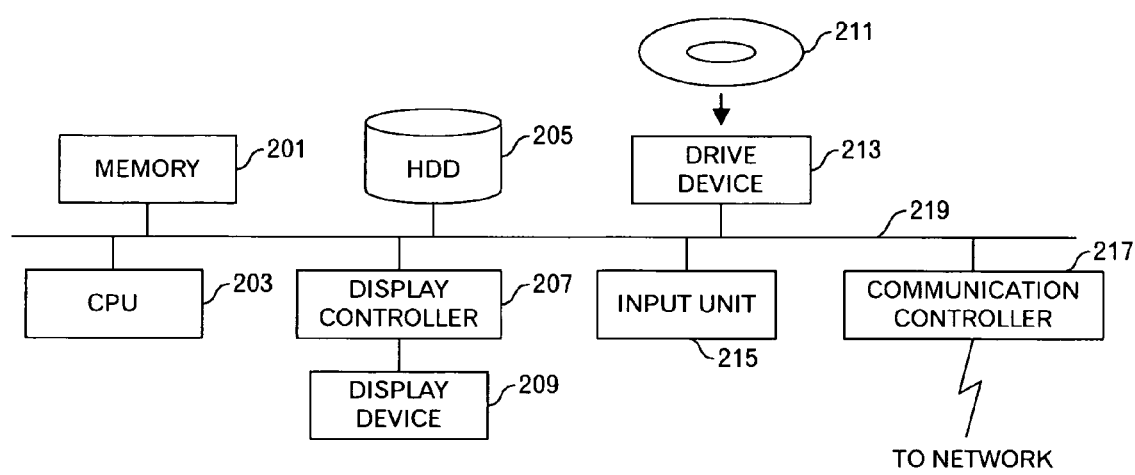
FIG. 12 is a functional block diagram of a computer.

Incidentally, the host computer 5, the sales terminal 7, and the maintenance terminal 9 are computer devices as shown in FIG. 12. That is, a memory (storage device) 201, a CPU (processor) 203, a hard disk drive (HDD) 205, a display controller 207 connected to a display device 209, a drive device 213 for a removal disk 211, an input device 215, and a communication controller 217 for connection with a network are connected through a bus 219 as shown in FIG. 28. An operating system (OS) and an application program for carrying out the foregoing processing in the embodiment, are stored in the HDD 205, and when executed by the CPU 203, they are read out from the HDD 205 to the memory 201. As the need arises, the CPU 203 controls the display controller 207, the communication controller 217, and the drive device 213, and causes them to perform necessary operations. Besides, intermediate processing data is stored in the memory 201, and if necessary, it is stored in the HDD 205. In this embodiment of this invention, the application program to realize the aforementioned functions is stored in the removal disk 211 and distributed, and then it is installed into the HDD 205 from the drive device 213. It may be installed into the HDD 205 via the network such as the Internet and the communication controller 217. In the computer as stated above, the hardware such as the CPU 203 and the memory 201, the OS and the necessary application program are systematically cooperated with each other, so that various functions as described above in details are realized.

In addition, as for the analysis apparatus 3, the function to carry out the analysis is the same as the conventional one, and the tag reader and writer 321 is provided for the reagent holder 32 to secure an interface with the RF tag 311. It is possible to realize the tag interface unit 33, the buffer 34, the analysis apparatus manager 35, the confirmation data storage 36, the operation state data storage 37, the order processor 39, the order log storage 40 and the network interface unit 38 by a computer apparatus as shown in FIG. 12.

Effect of this Invention

According to this invention, it becomes possible to appropriately manage the reagent.

In addition, as another aspect, it becomes possible to appropriately support the analysis so as to connect the reagent with the network.

DESCRIPTION OF SYMBOLS 1 network
3 analysis apparatus
5 host computer
7 sales staff terminal
9 maintenance staff terminal
11 LAN
31 reagent container
311 RF tag
32 reagent holder
321 tag reader and writer
322 sensor
33 tag interface unit
34 buffer
35 analysis apparatus manager
36 confirmation data storage
37 operation state data storage
38 network interface unit
39 order processor
40 order log storage
351 reagent usable/unusable judging unit 352 analysis result judging unit
51 communication controller
52 check unit
53 apparatus DB manager
54 reagent DB manager
55 order processor
56 order DB
57 result file storage
58 rule DB
59 apparatus DB
60 reagent DB
61 data update unit
62 inter-apparatus difference data generator
63 reagent trouble predictor
64 apparatus trouble predictor
65 inter-apparatus difference data storage
521 reagent check unit
522 apparatus check unit
523 analysis result check unit

The invention claimed is:

1. An analysis support method executed by an analysis system having an analysis apparatus and a remote computer, the analysis support method comprising:
reading reagent information concerning a reagent in a reagent container from a memory included in the reagent container, the reagent container being used by the analysis apparatus;
first judging whether the reagent in the reagent container is usable based on the read reagent information;
upon judging an unusable condition of the reagent by the first judging, writing data representing that the reagent is unusable into the memory included in the reagent container, and registering the data representing that the reagent is unusable into a reagent database managed by the remote computer connected with the analysis apparatus in association with identification information to identify the reagent container;
second judging whether there is an abnormal state for a specimen of an analysis using the reagent in the reagent container according to an abnormal detection condition for the specimen;
writing data relating to a result of the analysis of the specimen into the memory, the data relating to the result of the analysis of the specimen including information concerning a presence or absence of the abnormal state judged by the second judging; and
storing the data relating to the analysis of the specimen into an analysis result data storage managed by the remote computer.

2. The analysis support method as set forth in claim 1, further comprising:
upon judging a usable condition by the first judging, third judging, by the remote computer, whether the reagent in the reagent container is usable based on a condition identified from utilization results of reagents having a predetermined relation with the reagent in the reagent container; and
upon the third judging that the reagent in the reagent container is unusable, writing the data representing that the reagent is unusable into the memory included in the reagent container.

3. The analysis support method as set forth in claim 1, further comprising:
third judging, by the remote computer, whether the analysis apparatus is in an abnormal state based on analysis apparatus information concerning an operation state of the analysis apparatus.

4. The analysis support method as set forth in claim 1, further comprising:
third judging, by the remote computer, whether there is an abnormal state for an entire result of the analysis of the specimen by using the data relating to the result of the analysis for each specimen in a plurality of specimens.

5. The analysis support method as set forth in claim 4, further comprising:
upon the third judging of the abnormal state for the entire result of the analysis, presuming, by the remote computer, a cause of the abnormal state by using the data relating to the result of the analysis for each specimen in the plurality of specimens; and
presenting data concerning a presence or absence of the abnormal state for the entire result of the analysis and data concerning the presumed cause of the abnormal state for a user of the analysis apparatus.

6. An analysis support method executed by an analysis system having an analysis apparatus and a remote computer, said analysis support method comprising:
reading reagent information concerning a reagent in a reagent container from a memory included in the reagent container, the reagent container being used by the analysis apparatus;
first judging whether the reagent in the reagent container is usable based on the read reagent information;
upon judging an unusable condition of the reagent by the first judging, writing data representing that the reagent is unusable into the memory included in the reagent container, and registering the data representing that the reagent is unusable into a reagent database managed by the remote computer connected with the analysis apparatus in association with identification information to identify the reagent container;
writing data relating to a result of an analysis of a specimen using the reagent in the reagent container into the memory;
storing the data relating to the result of the analysis into an analysis result data storage managed by the remote computer; and
second judging whether there is an abnormal state for an entire result of the analysis of the specimen by using the data relating to the result of the analysis for each specimen in a plurality of specimens.

7. The analysis support method as set forth in claim 6, further comprising:
upon judging a usable condition by the first judging, third judging, by the remote computer, whether the reagent in the reagent container is usable based on a condition identified from utilization results of reagents having a predetermined relation with the reagent in the reagent container; and
upon the third judging that the reagent in the reagent container is unusable, writing the data representing that the reagent is unusable into the memory included in the reagent container.

8. The analysis support method as set forth in claim 7, further comprising:
fourth judging, by the remote computer, whether the analysis apparatus is in an abnormal state based on analysis apparatus information concerning an operation state of the analysis apparatus.

9. The analysis support method as set forth in claim 6, further comprising:
fifth judging, by the remote computer, whether there is an abnormal state according to an abnormal detection condition for the specimen of the analysis, and the data relating to the result of the analysis including information concerning a presence or absence of the abnormal state judged at the fifth judging.

10. The analysis support method as set forth in claim 6, further comprising:

upon the second judging that there is an abnormal state for the entire result of the analysis, presuming, by the remote computer, a cause of the abnormal state by using the data relating to the result of the analysis for each specimen in the plurality of specimens; and presenting data concerning a presence or absence of the abnormal state for the entire result of the analysis and data concerning the presumed cause of the abnormal state for a user of the analysis apparatus.

* * * * *